(12) United States Patent
Yan et al.

(10) Patent No.: US 8,993,258 B2
(45) Date of Patent: Mar. 31, 2015

(54) FLUORINATED VOLTAGE SENSITIVE DYES, PREPARATION THEREOF, AND OPTICAL METHODS OF USE

(71) Applicants: Ping Yan, Middletown, CT (US); Corey D. Acker, West Hartford, CT (US); Leslie M. Loew, West Hartford, CT (US)

(72) Inventors: Ping Yan, Middletown, CT (US); Corey D. Acker, West Hartford, CT (US); Leslie M. Loew, West Hartford, CT (US)

(73) Assignee: The University of Connecticut, Farmington, CT (US)

( * ) Notice: Subject to any disclaimer, the term of this patent is extended or adjusted under 35 U.S.C. 154(b) by 0 days.

(21) Appl. No.: 13/908,055

(22) Filed: Jun. 3, 2013

(65) Prior Publication Data

US 2013/0330762 A1 Dec. 12, 2013

Related U.S. Application Data

(60) Provisional application No. 61/658,442, filed on Jun. 12, 2012.

(51) Int. Cl.
| | | |
|---|---|---|
| C07D 213/38 | (2006.01) | |
| C07D 213/73 | (2006.01) | |
| G01N 21/66 | (2006.01) | |
| C09B 57/00 | (2006.01) | |

(52) U.S. Cl.
CPC ............. *C07D 213/38* (2013.01); *G01N 21/66* (2013.01); *C09B 57/00* (2013.01)
USPC ............. 435/29; 546/304; 546/307; 546/311; 546/312; 546/334

(58) Field of Classification Search
USPC ............... 435/29; 424/9.1, 9.6; 546/304, 307, 546/311, 329, 334
See application file for complete search history.

(56) References Cited

U.S. PATENT DOCUMENTS 7,034,044 B2 * 4/2006 Alanine et al. ................. 514/337
8,129,532 B2 3/2012 Loew et al.

FOREIGN PATENT DOCUMENTS

DE 102005025906 A1 12/2006

OTHER PUBLICATIONS

Leslie M. Lowe, Membrane Potential Imaging in the Nervous System: Methods and Applications-2010.*
C. D. Acker and S. D. Antic, 2009, Quantitative assessment of the distributions of membrane conductances involved in action potential backpropagation along basal dendrites, Journal of Neurophysiology, vol. 101, pp. 1524-1541.
C. D. Acker, P. Yan, and L. M. Loew, Single-Voxel Recording of Voltage Transients in Dendritic Spines, 2011, Biophysical Journal, vol. 101, pp. L11-L13.
S. D. Antic, 2003, Action potentials in basal and oblique dendrites of rat neocortical pyramidal neurons, Journal of Physiology-London, vol. 550, pp. 35-50.
J. A. N. Fisher, J. R. Barchi, C. G. Welle, G. H. Kim, P. Kosterin, A. L. Obaid, A. G. Yodh, D. Contreras, and B. M. Salzberg, 2008, Two-photon excitation of potentiometric probes enables optical recording of action potentials from mammalian nerve terminals in situ, Journal of Neurophysiology, vol. 99, pp. 1545-1553.
K. Holthoff, D. Zecevic, and A. Konnerth, 2010, Rapid time course of action potentials in spines and remote dendrites of mouse visual cortex neurons, The Journal of Physiology (London), vol. 588, pp. 1085 1096.
L. M. Loew, 1982, Design and characterization of electrochromic membrane probes, Journal of Biochemical and Biophysical Methods, vol. 6, pp. 243-260; B. Kuhn, P. Fromherz, and W. Denk, 2004, High sensitivity of stark-shift voltage-sensing dyes by one-or two-photon excitation near the red spectral edge, Biophysical Journal, vol. 87, pp. 631-639.
M. Nuriya, J. Jiang, B. Nemet, K. Eisenthal, and R. Yuste, Imaging membrane potential in dendritic spines, Proc. Natl. Acad. Sci. U.S. A., 2006, pp. 786-790.
L. M. Palmer and G. J. Stuart, 2009, Membrane Potential Changes in Dendritic Spines during Action Potentials and Synaptic Input, The Journal of Neuroscience, vol. 29, pp. 6897-6903.
Renikuntla et al., "Improved Photostability and Fluorescence Properties through Polyfluorination of a Cyanine Dye", Organic Letters, 2004, vol. 6, No. 6, pp. 909-912.
Sacconi et al., "Action potential propagation in transverse-axial tubular system is impaired in heart failure", PNAS, Apr. 10, 2012, vol. 109, No. 15, pp. 5815-5819.
G. Stuart, N. Spruston, B. Sakmann, and M. Häusser, 1997, Action potential initiation and back-propagation in neurons of the mammalian CNS, Trends in Neurosciences, vol. 20, pp. 125-131.

(Continued)

*Primary Examiner* — Michael G Hartley
*Assistant Examiner* — Jagadishwar Samala
(74) *Attorney, Agent, or Firm* — Cantor Colburn LLP

(57) ABSTRACT

A fluorinated voltage sensitive dye has the structure

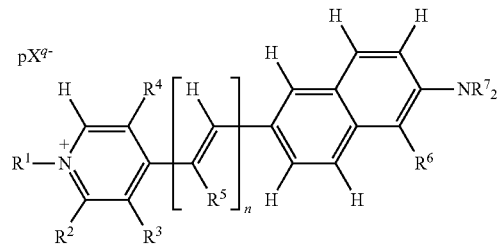

wherein p is 0, 1, or 2; $X^{q-}$ is an anionic counterion having a charge, q, that is 1 or 2; n is 1 or 2; $R^1$ is an optionally substituted $C_1$-$C_{12}$ alkyl; $R^2$ is hydrogen, and $R^3$ is hydrogen or fluorine; or $R^2$ and $R^3$ collectively form a divalent —CH=CH—CH=CH— group; $R^4$ and each occurrence of $R^5$ are each independently hydrogen or fluorine; $R^6$ is hydrogen or fluorine or trifluoromethyl; and each occurrence of $R^7$ is independently $C_1$-$C_6$ alkyl;
provided that the dye comprises at least one fluorine atom. The dye is particularly useful for monitoring the dynamics of action potentials in axons and/or dendrites.

24 Claims, 4 Drawing Sheets

(56) References Cited

OTHER PUBLICATIONS

G. J. Stuart and B. Sakmann, 1994, Active propagation of somatic action potentials into neocortical pyramidal cell dendrites, Naature, vol. 367, pp. 69-72.

Wang, Z. Lu, S. Lord, K. Willets, J. Bertke, S. Bunge, W. Moerner, and R. Twieg, 2007, The influence of tetrahydroquinoline rings in dicyanomethylenedihydrofuran (DCDHF) single-molecule fluorophores, Tetrahedron, pp. 103-114; P. Yan, A. Xie, M. Wei, and L. Loew, 2008.

P. Yan, A. Xie, M. Wei, and L. Loew, 2008, Amino(oligo)thiophene-based environmentally sensitive biomembrane chromophores, Journal of Organic Chemistry, pp. 6587-6594.

W. L. Zhou, P. Yan, J. P. Wuskell, L. M. Loew, and S. D. Antic, 2008, Dynamics of action potential back propagation in basal dendrites of prefrontal cortical pyramidal neurons, European Journal of Neuroscience, vol. 27, pp. 923-936.

* cited by examiner

FLUORINATED VOLTAGE SENSITIVE DYES, PREPARATION THEREOF, AND OPTICAL METHODS OF USE

CROSS REFERENCE TO RELATED APPLICATION

This application claims the benefit of U.S. Provisional Patent Application Ser. No. 61/658,442, filed Jun. 12, 2012, which is fully incorporated herein by reference.

STATEMENT REGARDING FEDERALLY SPONSORED RESEARCH & DEVELOPMENT

This invention was made with government support under Grant No. R01 EB001963 awarded by The National Institutes of Health. The government has certain rights in the invention.

BACKGROUND OF THE INVENTION

Voltage sensitive dye (VSD) imaging of electrical activity permits the high spatial resolution recording of voltage changes when classical electrodes or patch pipettes are too bulky. M. Canepari and D. Zecevic, editors, 2010, "Membrane Potential Imaging in the Nervous System Methods and Applications", Springer: New York. Perhaps the ultimate application of optical voltage recording, requiring excellent spatial and temporal resolution, is to probe voltage changes at individual dendritic spines, the fundamental neuronal units for the initial processing of synaptic inputs. This has been recently achieved using second harmonic generation (M. Nuriya, J. Jiang, B. Nemet, K. Eisenthal, and R. Yuste, 2006, "Imaging membrane potential in dendritic spines", Proc. Natl. Acad. Sci. U.S.A., pages 786-790), confocal linescans (L. M. Palmer and G. J. Stuart, 2009, "Membrane Potential Changes in Dendritic Spines during Action Potentials and Synaptic Input", The Journal of Neuroscience, volume 29, pages 6897-6903) and a fast CCD camera (K. Holthoff, D. Zecevic, and A. Konnerth, 2010, "Rapid time course of action potentials in spines and remote dendrites of mouse visual cortex neurons", The Journal of Physiology (London), volume 588, pages 1085-1096) to image spines near the surface of a brain slice. In each case, the VSD was applied intracellularly and allowed to diffuse into the dendritic arbor. In the latter study, a dramatic increase in sensitivity and signal-to-noise permitted visualization of spine voltage changes in single trials. Applying this approach to 2-photon imaging of VSDs (J. A. N. Fisher, J. R. Barchi, C. G. Welle, G. H. Kim, P. Kosterin, A. L. Obaid, A. G. Yodh, D. Contreras, and B. M. Salzberg, 2008, "Two-photon excitation of potentiometric probes enables optical recording of action potentials from mammalian nerve terminals in situ", Journal of Neurophysiology, volume 99, pages 1545-1553) could improve the measurements still further by permitting deeper penetration of the brain while preserving the sensitivity of fluorescence-based detection.

BRIEF SUMMARY OF EMBODIMENTS OF THE INVENTION

Here we introduce a new VSD optimized for 2-photon imaging, combining it with a single voxel recording method targeted to individual spines. This combination allowed us to obtain recordings with sufficient temporal resolution to record fast voltage transients in single spines with "single sweep" sensitivity. We use this approach to examine how back-propagating action potentials (bAPs) recorded in spines vary at different locations along the dendritic tree of a pyramidal neuron in a mouse cortical brain slice.

One embodiment is a fluorinated voltage sensitive dye having the structure

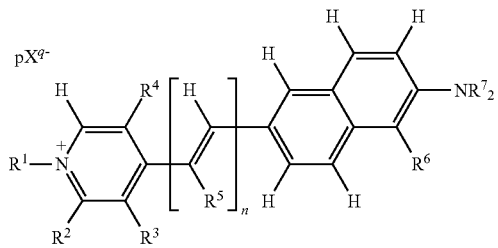

wherein p is 0, 1, or 2; $X^{q-}$ is an anionic counterion having a charge, q, that is 1 or 2; n is 1 or 2; $R^1$ is an optionally substituted $C_1$-$C_{12}$ alkyl; $R^2$ is hydrogen, and $R^3$ is hydrogen or fluorine; or $R^2$ and $R^3$ collectively form a divalent —CH=CH—CH=CH— group; $R^4$ and each occurrence of $R^5$ are each independently hydrogen or fluorine; $R^6$ is hydrogen or fluorine or trifluoromethyl; and each occurrence of $R^7$ is independently $C_1$-$C_6$ alkyl; provided that the dye comprises at least one fluorine atom.

Another embodiment is a method of forming a fluorinated voltage sensitive dye, the method comprising: reacting a 1-(optionally substituted $C_1$-$C_{12}$ alkyl)-4-methylpyridinium compound and a 6-dialkylaminonaphthalene-2-carboxaldehyde to form the fluorinated voltage sensitive dye; wherein the 1-(optionally substituted $C_1$-$C_{12}$ alkyl)-4-methylpyridinium compound has the structure

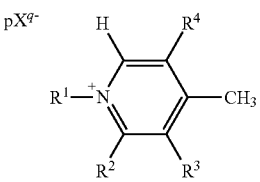

wherein p is 0, 1, or 2; $X^{q-}$ is an anionic counterion having a charge, q, that is 1 or 2; $R^1$ is an optionally substituted $C_1$-$C_{12}$ alkyl; $R^2$ is hydrogen, and $R^3$ is hydrogen or fluorine; or $R^2$ and $R^3$ collectively form a divalent —CH=CH—CH=CH— group; and $R^4$ is hydrogen or fluorine;
wherein the 6-dialkylaminonaphthalene-2-carboxaldehyde has the structure

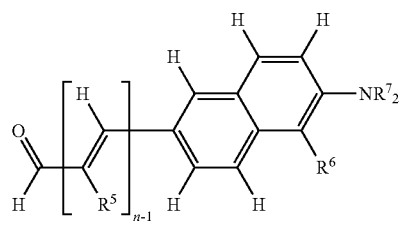

wherein n is 1 or 2; each occurrence of $R^5$ is independently hydrogen or fluorine; $R^6$ is hydrogen or fluorine or trifluoromethyl; and each occurrence of $R^7$ is independently $C_1$-$C_6$ alkyl; and wherein the fluorinated voltage sensitive dye has the structure

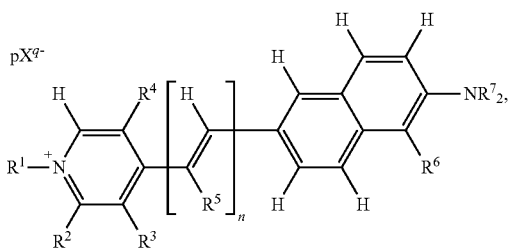

wherein p, $X^{q-}$, n, and $R^1$-$R^7$ are as defined above, and the dye comprises at least one fluorine atom.

Another embodiment is a method utilizing the fluorinated voltage sensitive dye for the optical assessment, monitoring, and/or evaluation of electrophysiology of organelles, cells, or tissues.

These and other embodiments are described in detail below.

DETAILED DESCRIPTION OF THE INVENTION

Figure 1:
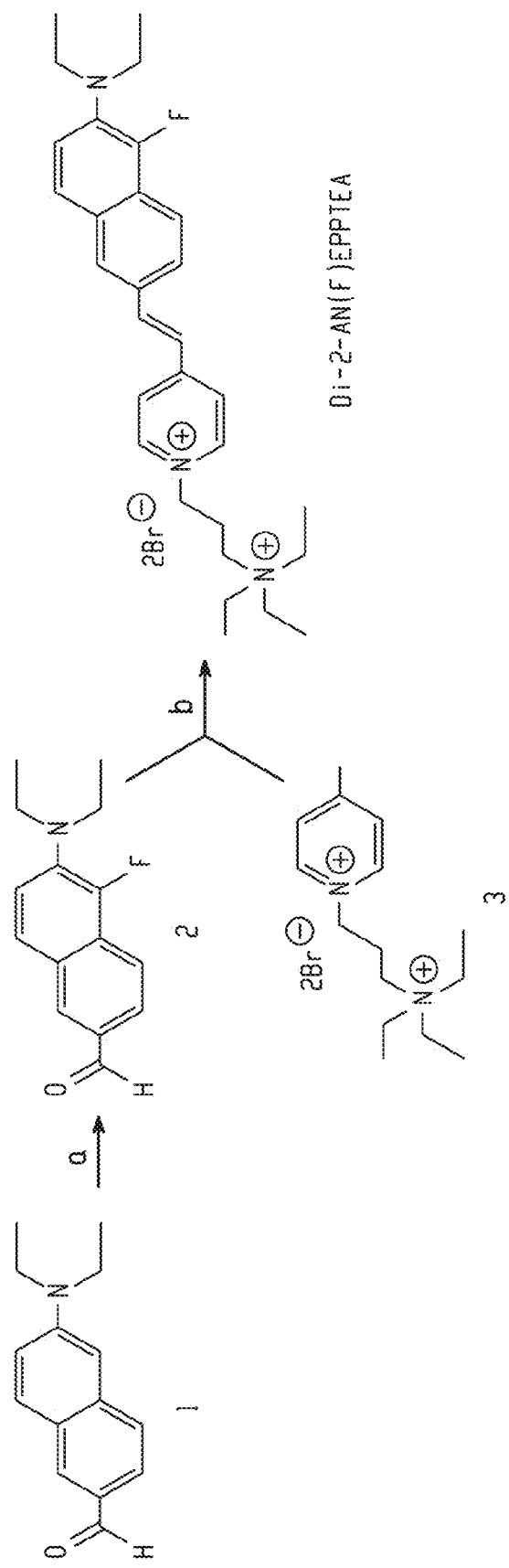
FIG. 1 is a chemical scheme for the synthesis of the dye designated di-2-AN(F)EPPTEA.

The present inventors have determined that certain selectively fluorinated dyes are sensitive probes for electrical activity in dendritic spines.

One embodiment is a fluorinated voltage sensitive dye having the structure

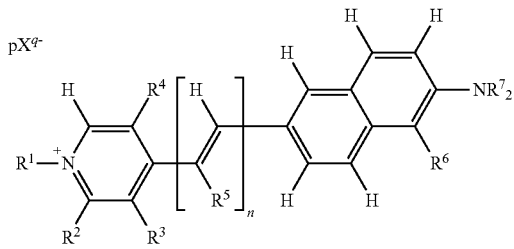

wherein p is 0, 1, or 2; $X^{q-}$ is an anionic counterion having a charge, q, that is 1 or 2; n is 1 or 2; $R^1$ is an optionally substituted $C_1$-$C_{12}$ alkyl; $R^2$ is hydrogen, and $R^3$ is hydrogen or fluorine; or $R^2$ and $R^3$ collectively form a divalent —CH=CH—CH=CH— group; $R^4$ and each occurrence of $R^5$ are each independently hydrogen or fluorine; $R^6$ is hydrogen or fluorine or trifluoromethyl; and each occurrence of $R^7$ is independently $C_1$-$C_6$ alkyl; provided that the dye comprises at least one fluorine atom. As used herein, the term "optionally substituted" means that any unspecified group bonded to carbon can be a hydrogen atom or a substituent such as, for example, halogen (including fluorine, chlorine, bromine, or iodine), hydroxyl, sulfonate, amino, dialkylamino, trialkylammonium, carboxylate, acryloyl, succinimide, maleimide, iodoacetamide, and the like.

The dye can include one or more counterions, $X^{q-}$, to balance any positive charge(s) on the remainder of the dye (including any charged substituents at $R^1$). In other words, the total negative charge, p×q, contributed by the anion(s) $pX^{q-}$, is equal to the net positive charge on the remainder of the dye. Suitable counterions, $X^{q-}$, include, for example, hydroxide, fluoride, chloride, bromide, iodide, sulfite, sulfate, acetate, trifluoroacetate, propionate, succinate, glycolate, stearate, lactate, malate, tartrate, citrate, ascorbate, pamoate, maleate, hydroxymaleate, phenylacetate, glutamate, benzoate, salicylate, sulfanilate, 2-acetoxybenzoate, fumarate, toluenesulfonate, methanesulfonate, ethanesulfonate, ethane disulfonate, benzenesulfonate, toluenesulfonate, oxalate, malonate, succinate, glutarate, adipate, isethionate, and the like, and mixtures thereof. In some embodiments, $X^{q-}$ is bromide.

In other embodiments, the dye is zwitterionic and includes no counterions, $X^{q-}$. For example, the dye is zwitterionic when $R^1$ is —$(CH_2)_3SO_3^-$ or —$(CH_2)_4SO_3^-$.

In the generic dye structure above, $R^1$ is an optionally substituted $C_1$-$C_{12}$ alkyl. Specific examples of $R^1$ substituents include —$CH_2CH(OH)CH_2N^+(CH_3)_2(CH_2CH_2OH)$, —$(CH_2)_3SO_3^-$, —$(CH_2)_4SO_3^-$, —$(CH_2)_3$—$N^+(R^8)_3$ wherein each occurrence of $R^8$ is independently $C_1$-$C_6$ alkyl, and —$(CH_2)_2$—$N^+(R^9)_3$ wherein each occurrence of $R^9$ is independently $C_1$-$C_6$ alkyl. In some embodiments, $R^1$ is —$(CH_2)_3$—$N^+(R^8)_3$ wherein each occurrence of $R^8$ is independently $C_1$-$C_6$ alkyl (e.g., ethyl).

In some embodiments, both $R^2$ and $R^3$ are hydrogen. In other embodiments, $R^2$ is hydrogen and $R^3$ is fluorine. In still other embodiments, $R^2$ and $R^3$ collectively form a divalent —CH=CH—CH=CH— group, so that the pyridinium ring becomes a quinolinium ring.

$R^4$ can be hydrogen or fluorine. In some embodiments, $R^4$ is hydrogen.

Each occurrence of $R^5$ can be hydrogen or fluorine. In some embodiments, n is 1 and $R^5$ is hydrogen. In other embodiments, n is 1 and $R^5$ is fluorine. In still other embodiments, n is 2 and each occurrence of $R^5$ is hydrogen. In yet other embodiments, n is 2 and one occurrence of $R^5$ is hydrogen and the other occurrence of $R^5$ is fluorine.

$R^6$ can be hydrogen or fluorine or trifluoromethyl (—$CF_3$). In some embodiments, $R^6$ is hydrogen. In other embodiments, $R^6$ is fluorine. In still other embodiments, $R^6$ is trifluoromethyl.

Each occurrence of $R^7$ is independently $C_1$-$C_6$ alkyl. In some embodiments, each occurrence of $R^7$ is ethyl. In other embodiments, each occurrence of $R^7$ is n-butyl.

The dye comprises at least one fluorine atom. In some embodiments, the dye comprises no more than four fluorine atoms. In some embodiments, the dye comprises four fluorine atoms. In some embodiments, the dye comprises three fluorine atoms. In some embodiments, the dye comprises two fluorine atoms. In some embodiments, the dye comprises one fluorine atom.

In a very specific embodiment, $pX^{q-}$ is $2Br^-$; n is 1; $R^1$ is —$(CH_2)_3$—$N^+(CH_2CH_3)_3$; $R^2$, $R^3$, $R^4$, and $R^5$ are hydrogen; $R^6$ is fluorine; and each occurrence of $R^7$ is ethyl, or each occurrence of $R^7$ is n-butyl. When $R^7$ is ethyl, the dye is designated di-2-AN(F)EPPTEA. When $R^7$ is n-butyl, the dye is designated di-4-AN(F)EPPTEA.

In some embodiments, the fluorinated voltage sensitive dye is selected from the group consisting of

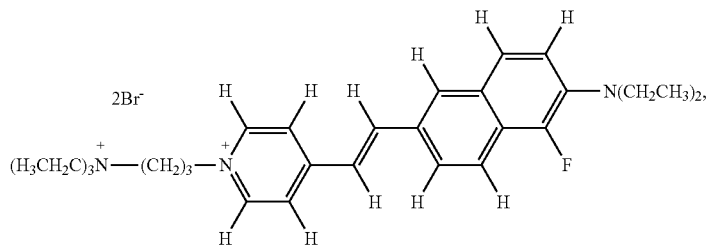

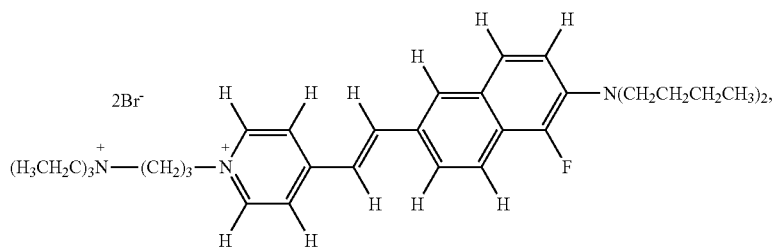

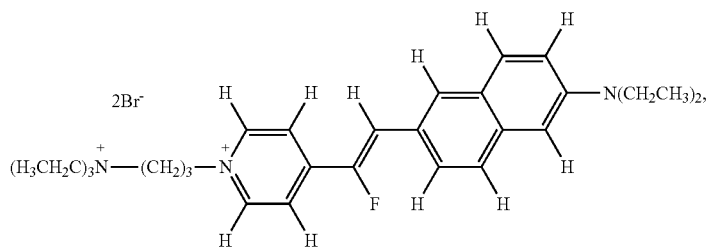

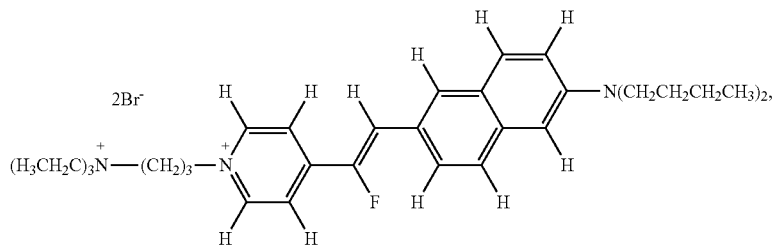

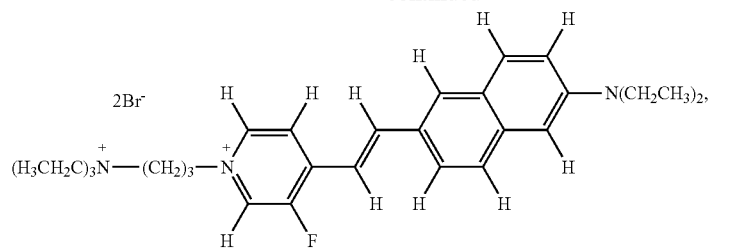
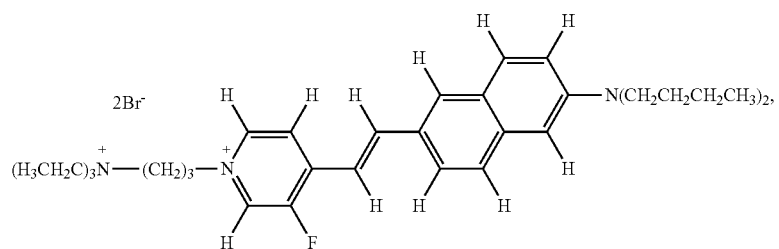
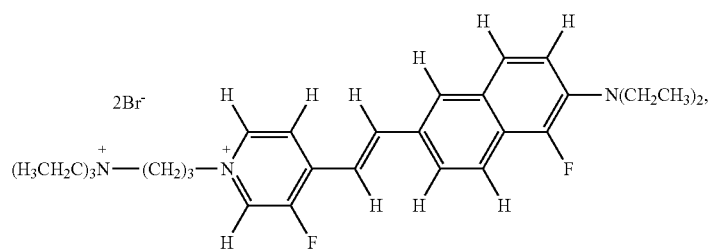
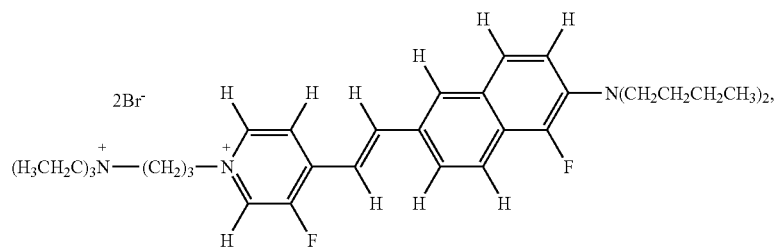
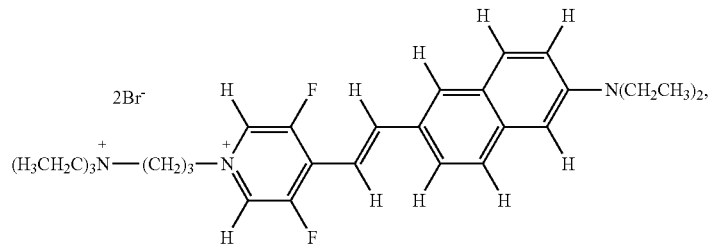
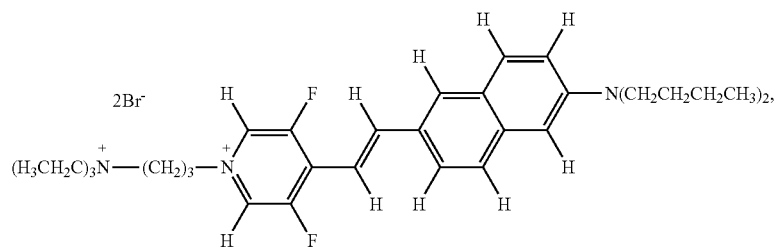

-continued
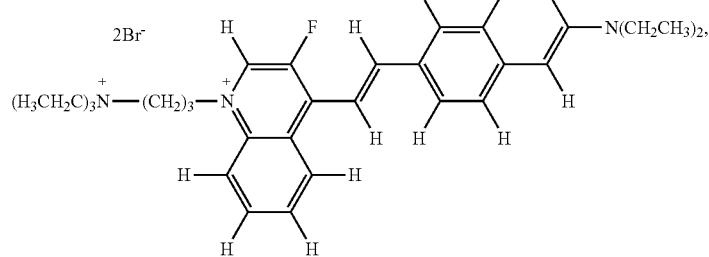
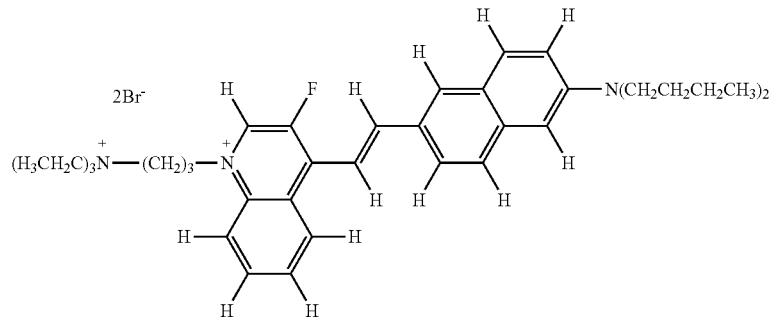
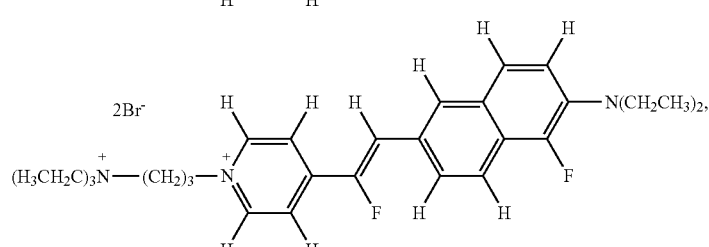
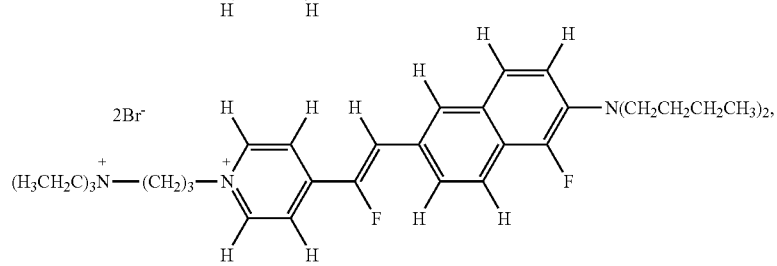
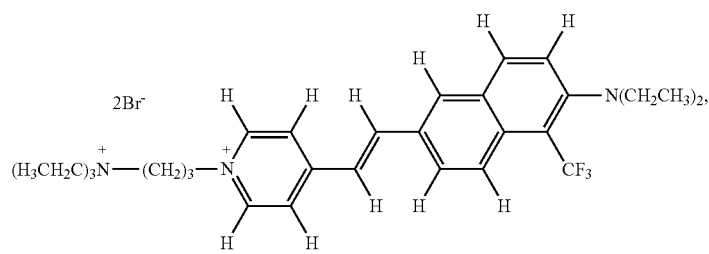
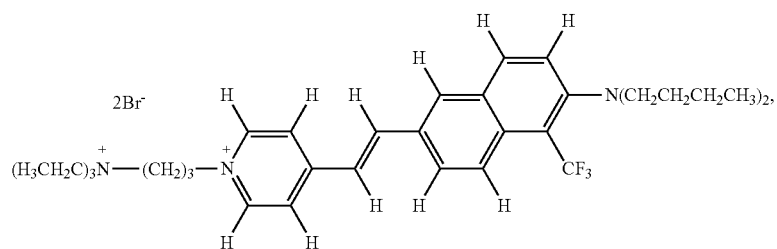

-continued
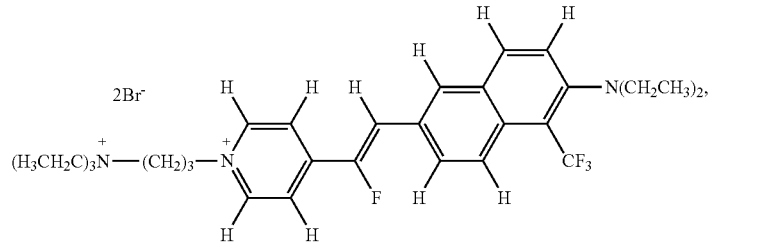
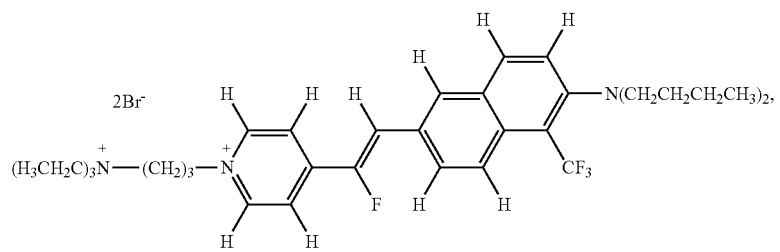
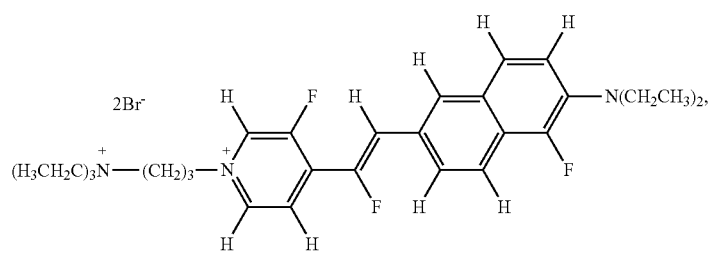
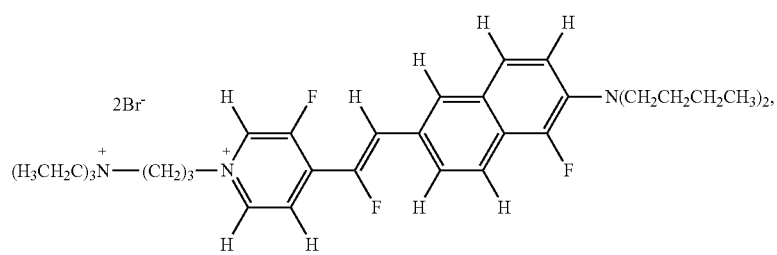
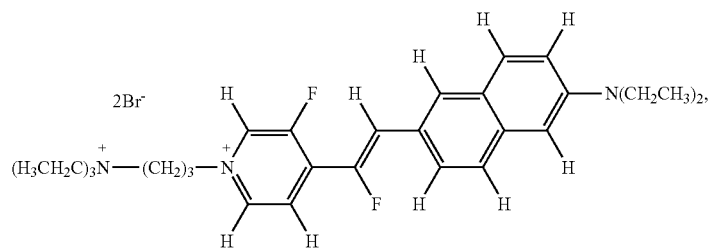
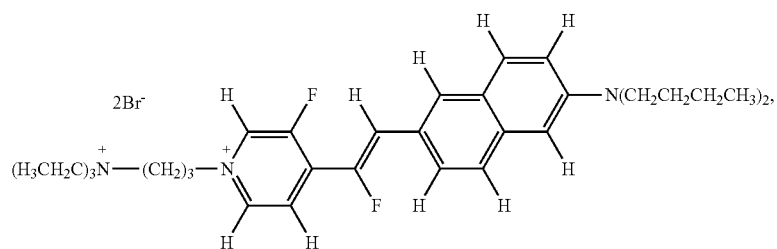

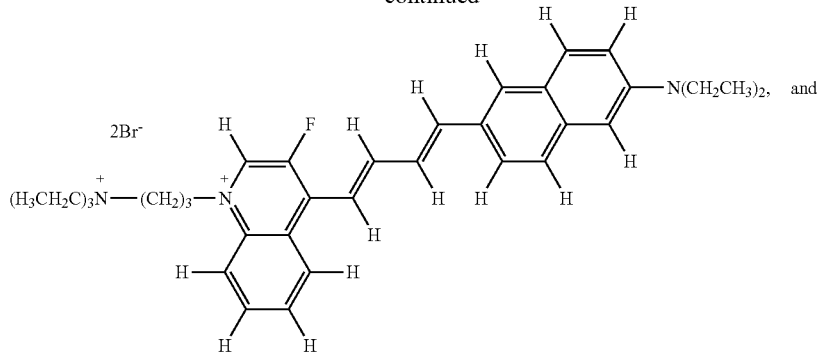
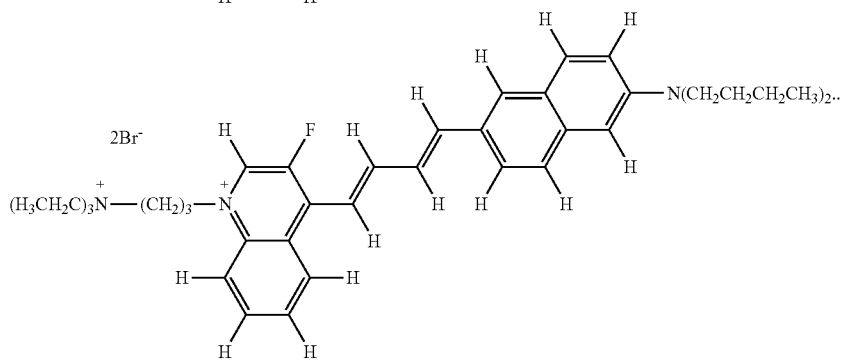
In some embodiments, the fluorinated voltage sensitive dye is selected from the group consisting of
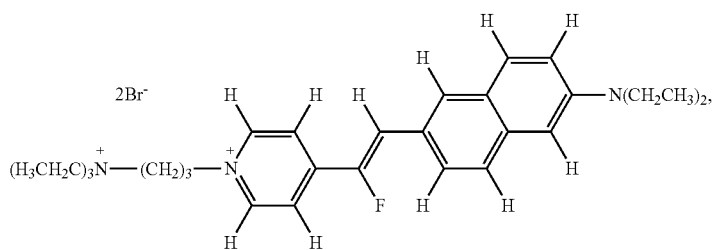
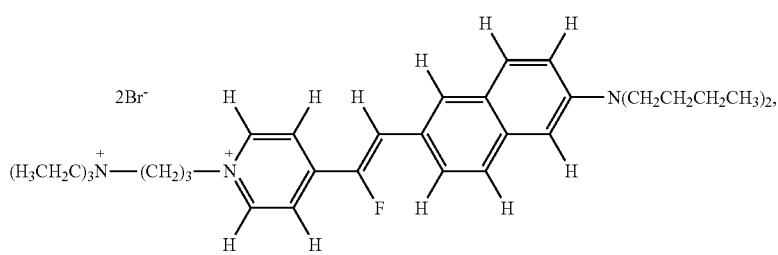
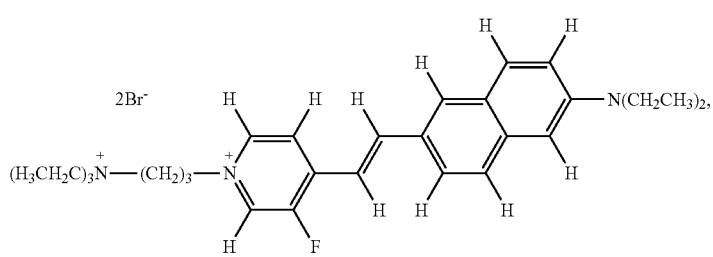

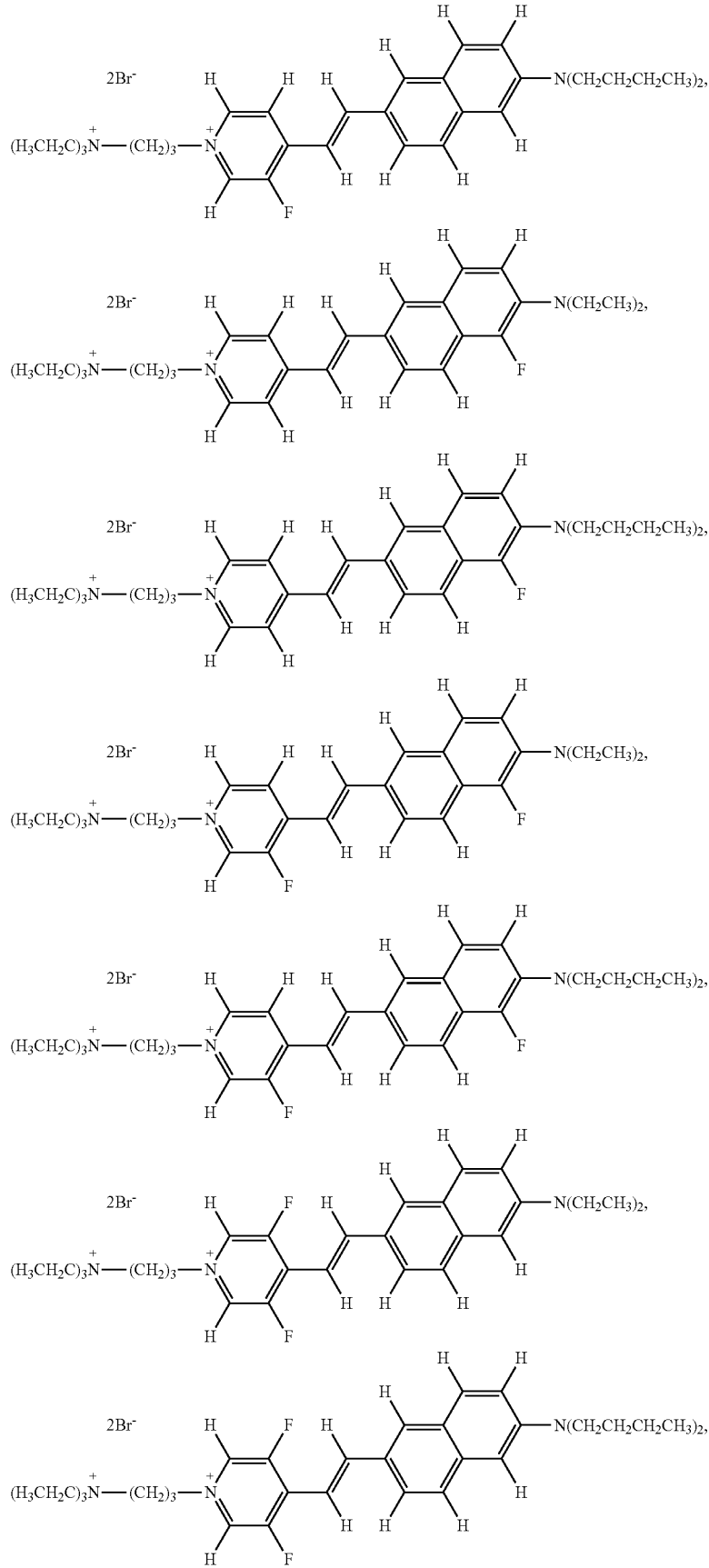

-continued
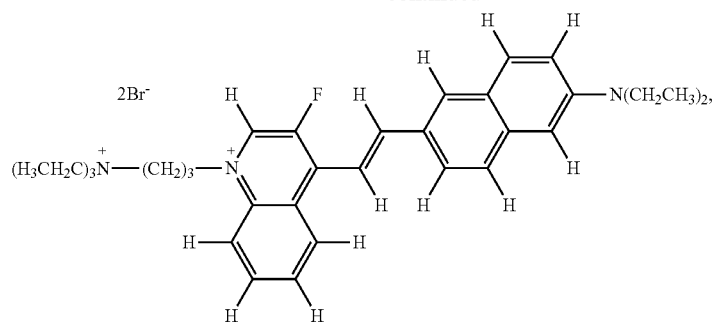
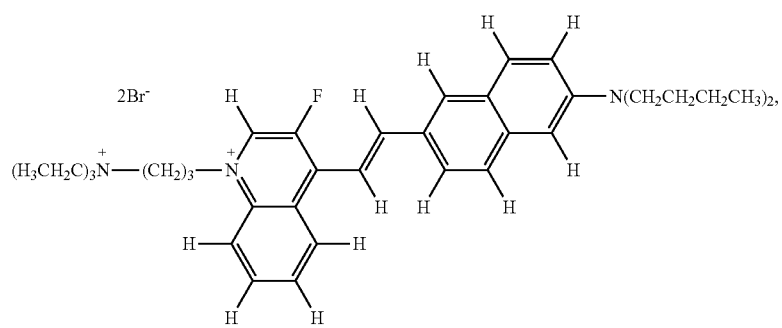
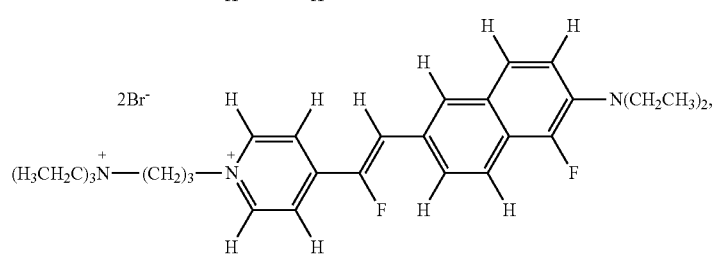
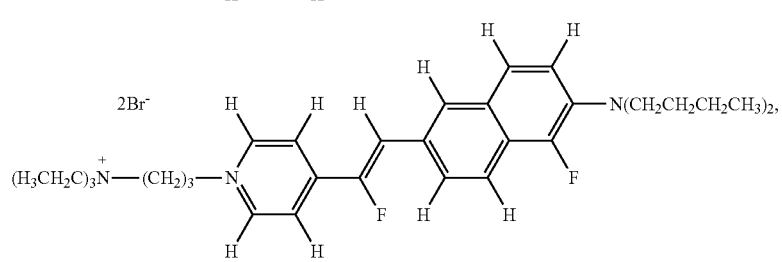
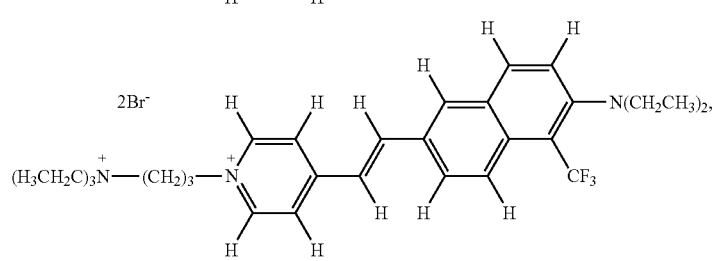
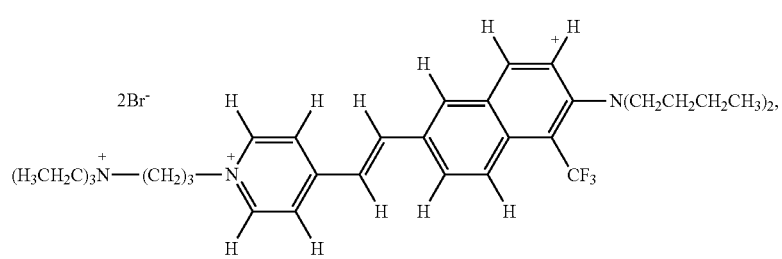

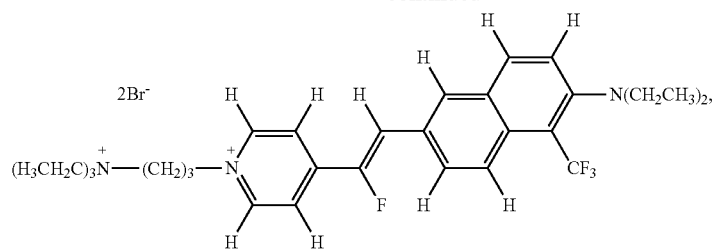
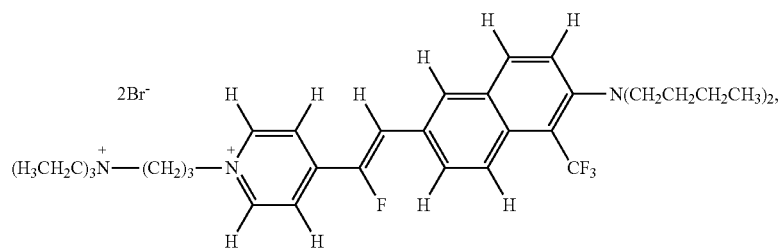
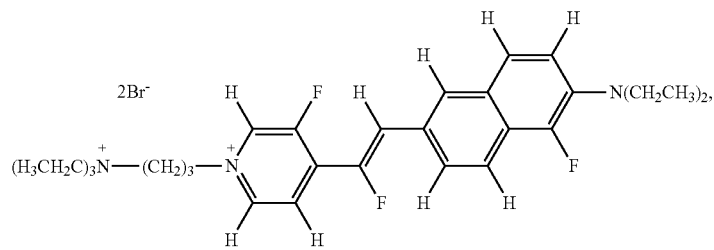
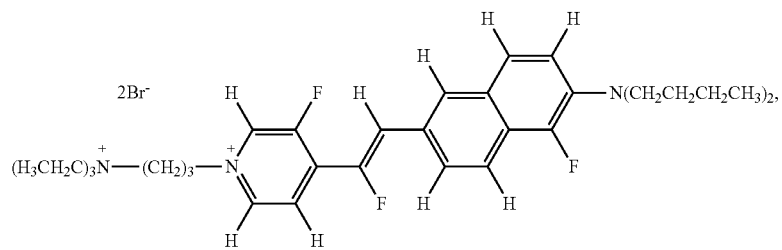
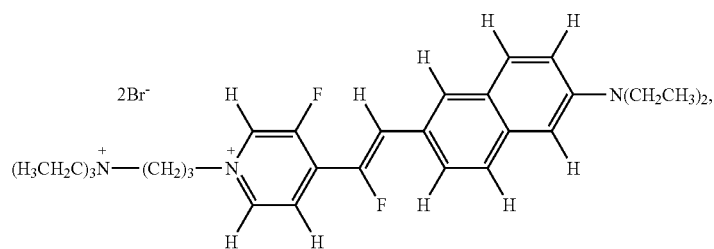
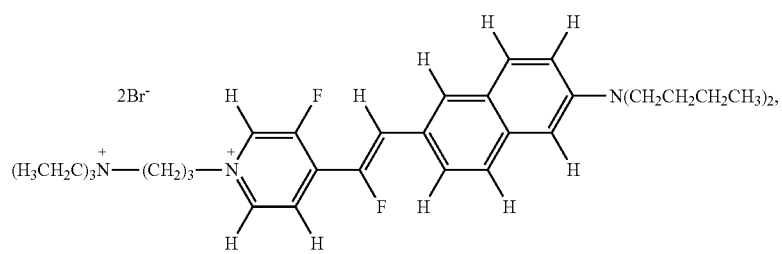

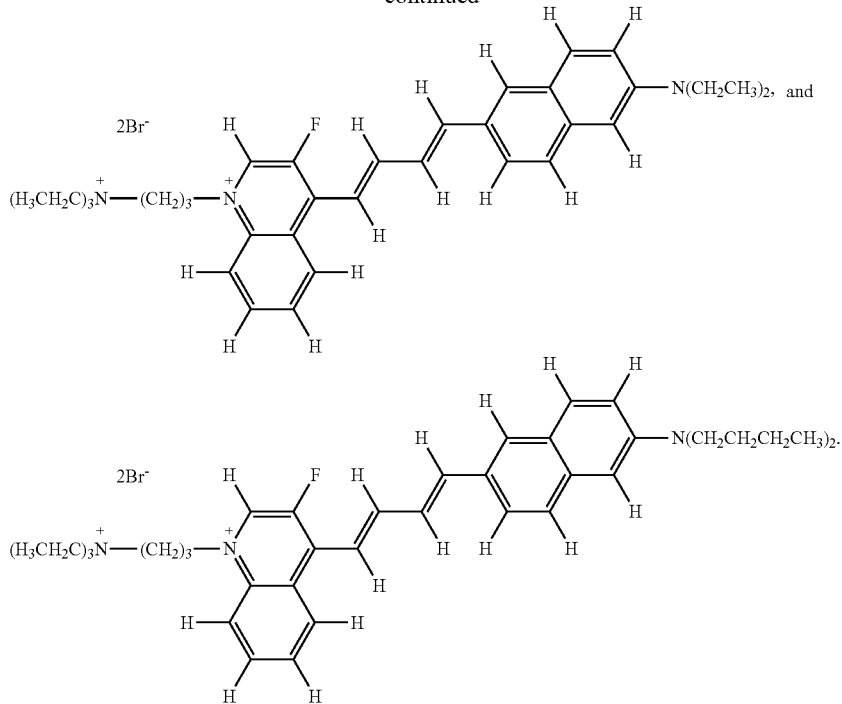

The invention includes a method of preparing the fluorinated voltage sensitive dye. Specifically, the method comprises reacting a 1-(optionally substituted $C_1$-$C_{12}$ alkyl)-4-methylpyridinium compound and a 6-dialkylaminonaphthalene-2-carboxaldehyde to form the fluorinated voltage sensitive dye; wherein the 1-(optionally substituted $C_1$-$C_{12}$ alkyl)-4-methylpyridinium compound has the structure

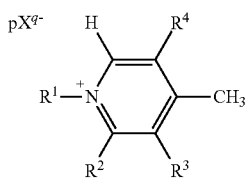

wherein p is 0, 1, or 2; $X^{q-}$ is an anionic counterion having a charge, q, that is 1 or 2; $R^1$ is an optionally substituted $C_1$-$C_{12}$ alkyl; $R^2$ is hydrogen, and $R^3$ is hydrogen or fluorine; or $R^2$ and $R^3$ collectively form a divalent —CH=CH—CH=CH— group; and $R^4$ is hydrogen or fluorine; wherein the 6-dialkylaminonaphthalene-2-carboxaldehyde has the structure

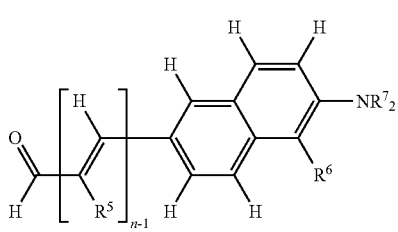

wherein n is 1 or 2; each occurrence of $R^5$ is independently hydrogen or fluorine; $R^6$ is hydrogen or fluorine or trifluoromethyl; and each occurrence of $R^7$ is independently $C_1$-$C_6$ alkyl; and wherein the fluorinated voltage sensitive dye has the structure

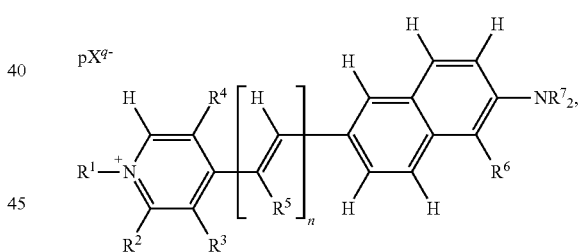

wherein p, $X^{q-}$, n, and $R^1$-$R^7$ are as defined above, and the dye comprises at least one fluorine atom.

The dye is useful as a spectroscopic and electrochemical probe of biological processes. Thus, one embodiment is a method utilizing a fluorinated voltage sensitive dye of claim 1 for the optical assessment, monitoring, and/or evaluation of electrophysiology of organelles, cells, or tissues. In some embodiments, the method includes monitoring a change in wavelength and/or intensity of a fluorescence emission from one-photon excitation or two-photon excitation of the fluorinated voltage sensitive dye. In some embodiments, the method includes monitoring the dynamics of action potentials in axons and/or dendrites. The extreme sensitivity of the method permits monitoring the dynamics of action potentials in an individual dendritic spine.

The invention includes at least the following embodiments.

Embodiment 1: A fluorinated voltage sensitive dye having the structure

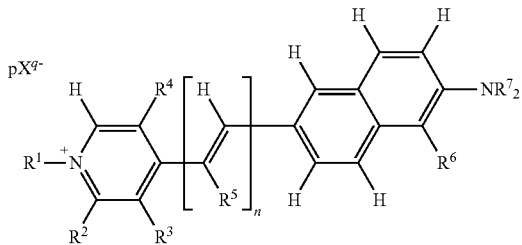

wherein p is 0, 1, or 2; $X^{q-}$ is an anionic counterion having a charge, q, that is 1 or 2; n is 1 or 2; $R^1$ is an optionally substituted $C_1$-$C_{12}$ alkyl; $R^2$ is hydrogen, and $R^3$ is hydrogen or fluorine; or $R^2$ and $R^3$ collectively form a divalent —CH=CH—CH=CH— group; $R^4$ and each occurrence of $R^5$ are each independently hydrogen or fluorine; $R^6$ is hydrogen or fluorine or trifluoromethyl; and each occurrence of $R^7$ is independently $C_1$-$C_6$ alkyl; provided that the dye comprises at least one fluorine atom.

Embodiment 2: The fluorinated voltage sensitive dye of embodiment 1, wherein $X^{q-}$ is $Br^-$.

Embodiment 3: The fluorinated voltage sensitive dye of embodiment 1 or 2, wherein n is 1.

Embodiment 4: The fluorinated voltage sensitive dye of embodiment 1 or 2, wherein n is 2.

Embodiment 5: The fluorinated voltage sensitive dye of any of embodiments 1-4, wherein $R^1$ is selected from the group consisting of —$CH_2CH(OH)CH_2N^+(CH_3)_2$ ($CH_2CH_2OH$), —$(CH_2)_3SO_3^-$, —$(CH_2)_4SO_3^-$, —$(CH_2)_3$—$N^+(R^8)_3$ wherein each occurrence of $R^8$ is independently $C_1$-$C_6$ alkyl, and —$(CH_2)_2$—$N^+(R^9)_3$ wherein each occurrence of $R^9$ is independently $C_1$-$C_6$ alkyl.

Embodiment 6: The fluorinated voltage sensitive dye of any of embodiments 1-5, wherein $R^1$ is —$(CH_2)_3$—$N^+(R^8)_3$ wherein each occurrence of $R^8$ is independently $C_1$-$C_6$ alkyl.

Embodiment 7: The fluorinated voltage sensitive dye of any of embodiments 1-6, wherein $R^2$ and $R^3$ are hydrogen.

Embodiment 8: The fluorinated voltage sensitive dye of any of embodiments 1-6, wherein $R^2$ is hydrogen and $R^3$ is fluorine.

Embodiment 9: The fluorinated voltage sensitive dye of any of embodiments 1-6, wherein $R^2$ and $R^3$ collectively form a divalent —CH=CH—CH=CH— group.

Embodiment 10: The fluorinated voltage sensitive dye of any of embodiments 1-9, wherein $R^4$ is hydrogen.

Embodiment 11: The fluorinated voltage sensitive dye of any of embodiments 1-10, wherein n is 1, and $R^5$ is hydrogen.

Embodiment 12: The fluorinated voltage sensitive dye of any of embodiments 1-10, wherein n is 1, and $R^5$ is fluorine.

Embodiment 13: The fluorinated voltage sensitive dye of any of embodiments 1-10, wherein n is 2, and each occurrence of $R^5$ is hydrogen.

Embodiment 14: The fluorinated voltage sensitive dye of any of embodiments 1-10, wherein n is 2, and one occurrence of $R^5$ is hydrogen and the other occurrence of $R^5$ is fluorine.

Embodiment 15: The fluorinated voltage sensitive dye of any of embodiments 1-14, wherein each occurrence of $R^7$ is ethyl, or each occurrence of $R^7$ is n-butyl.

Embodiment 16: The fluorinated voltage sensitive dye of any of embodiments 1-15, wherein the dye comprises no more than four fluorine atoms.

Embodiment 17: The fluorinated voltage sensitive dye of any of embodiments 1-16, wherein the dye comprises four fluorine atoms.

Embodiment 18: The fluorinated voltage sensitive dye of any of embodiments 1-16, wherein the dye comprises three fluorine atoms.

Embodiment 19: The fluorinated voltage sensitive dye of any of embodiments 1-16, wherein the dye comprises two fluorine atoms.

Embodiment 20: The fluorinated voltage sensitive dye of any of embodiments 1-16, wherein the dye comprises one fluorine atom.

Embodiment 21: The fluorinated voltage sensitive dye of embodiment 1, wherein $pX^{q-}$ is $2Br^-$; n is 1; $R^1$ is —$(CH_2)_3$—$N^+(CH_2CH_3)_3$; $R^2$, $R^3$, $R^4$, and $R^5$ are hydrogen; $R^6$ is fluorine; and each occurrence of $R^7$ is ethyl, or each occurrence of $R^7$ is n-butyl.

Embodiment 22: The fluorinated voltage sensitive dye of embodiment 1, selected from the group consisting of

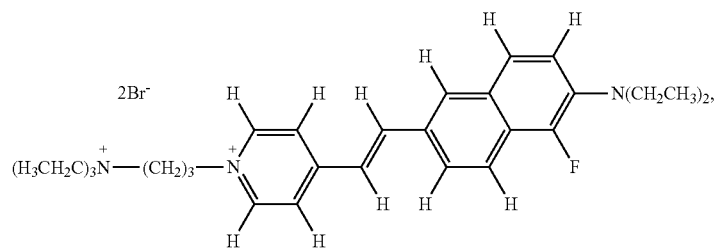

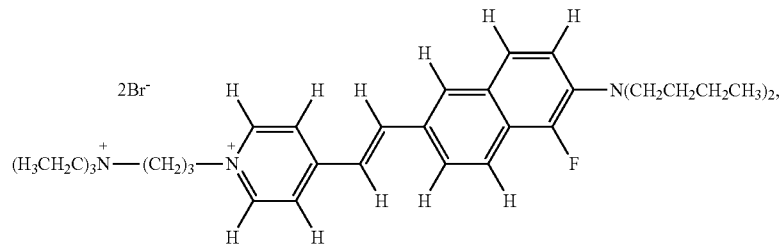

-continued
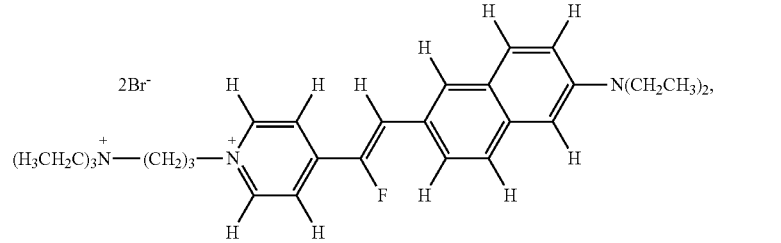
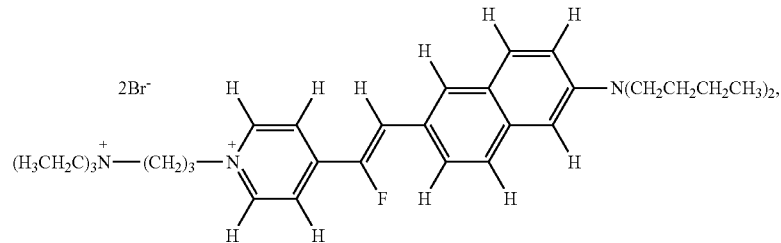
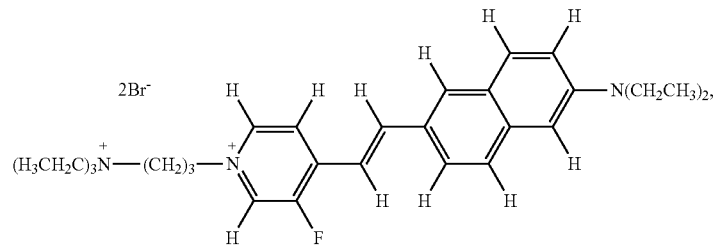
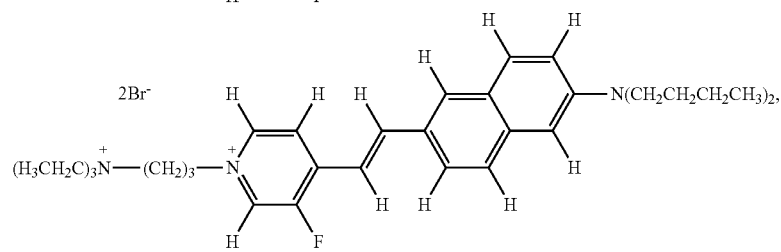
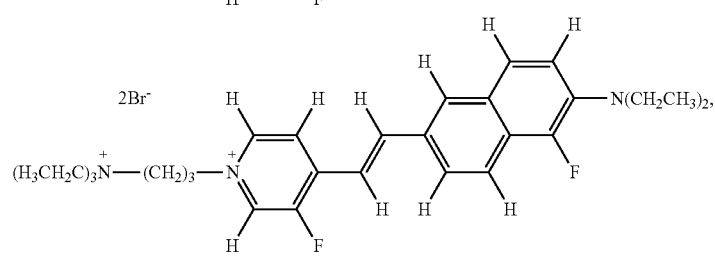
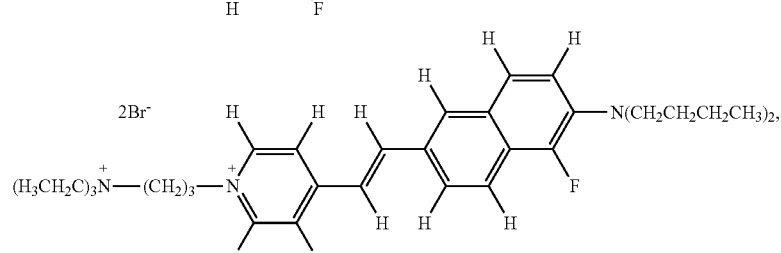
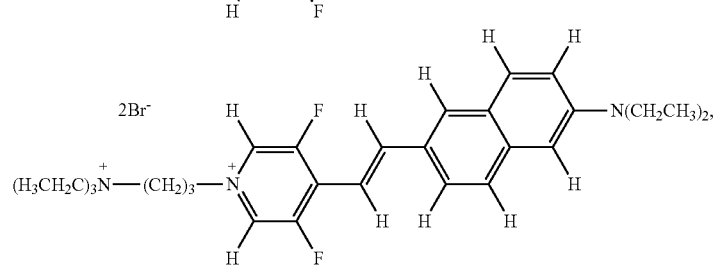

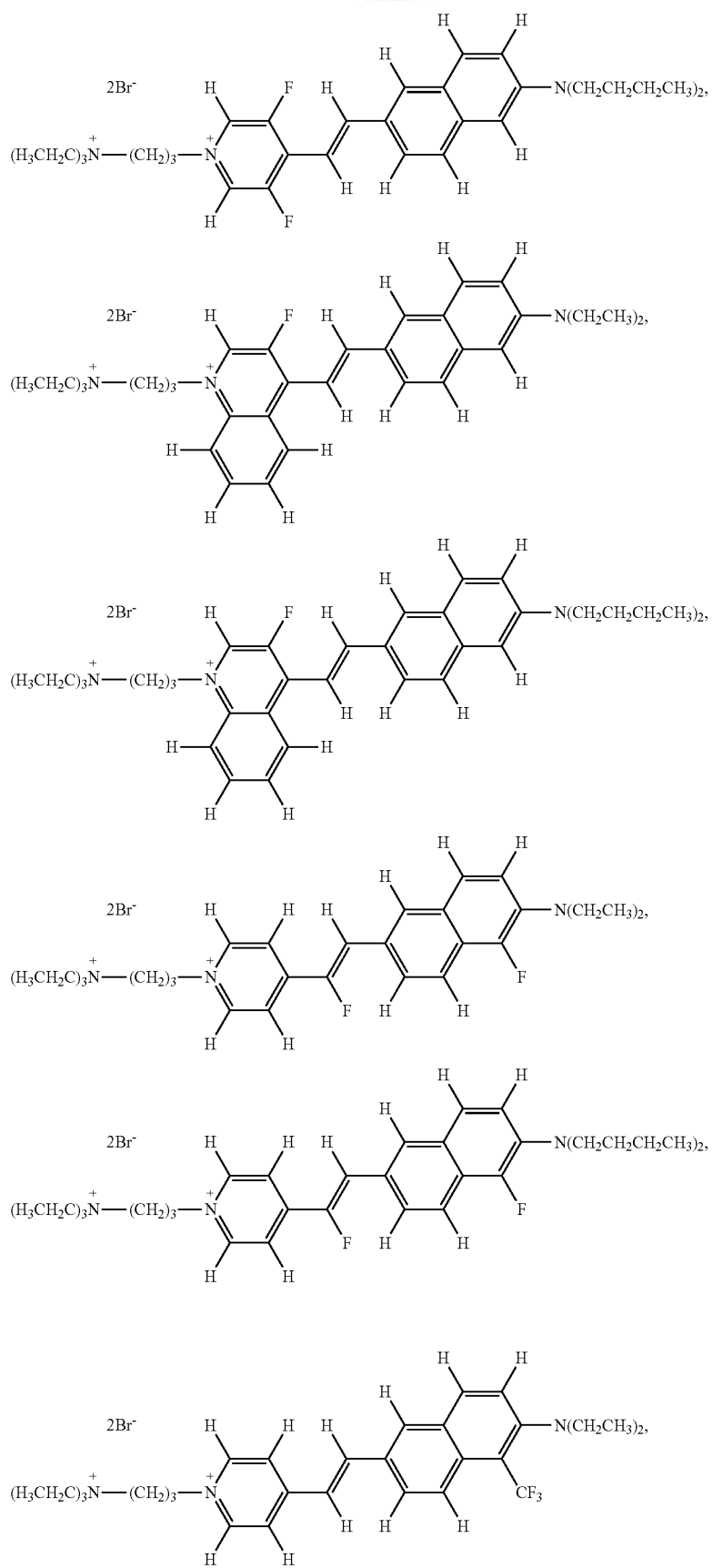

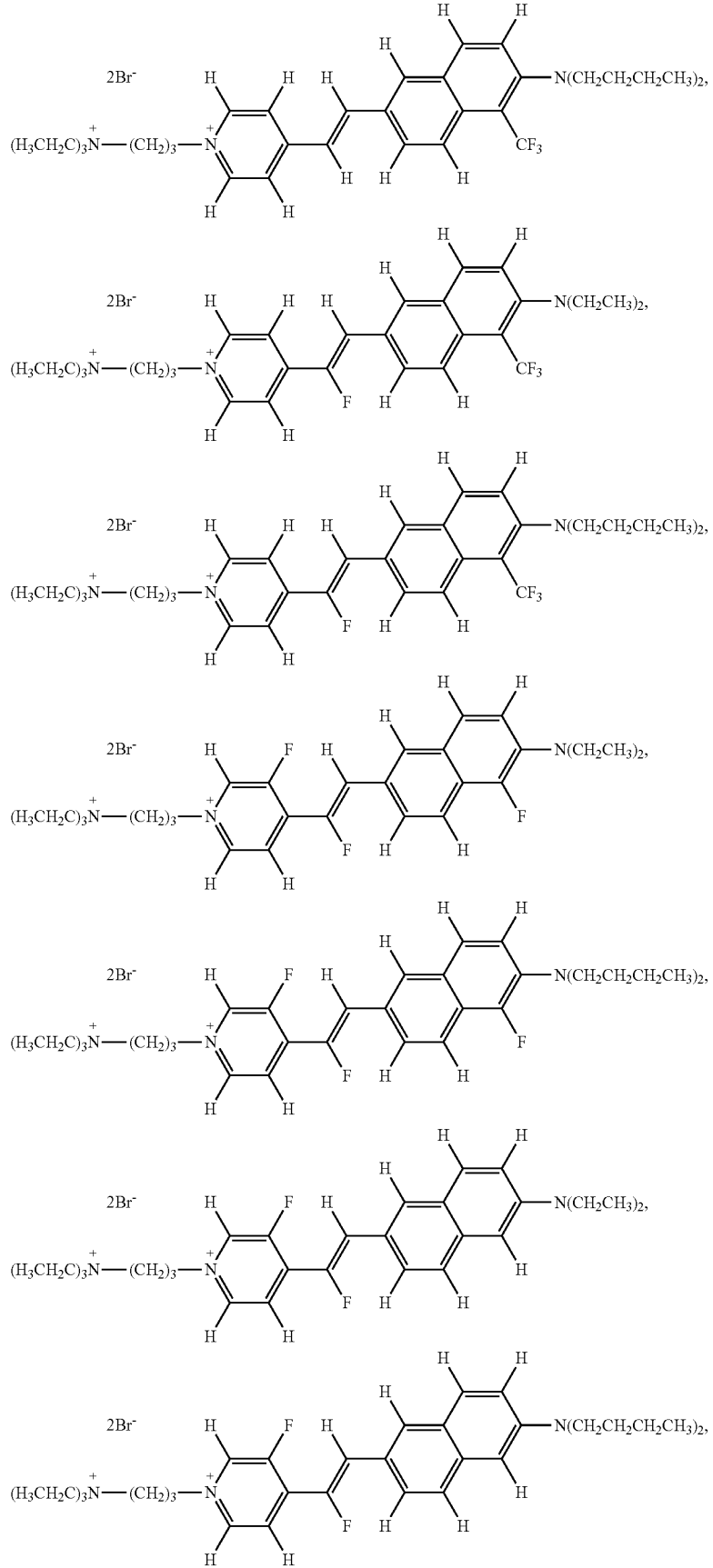

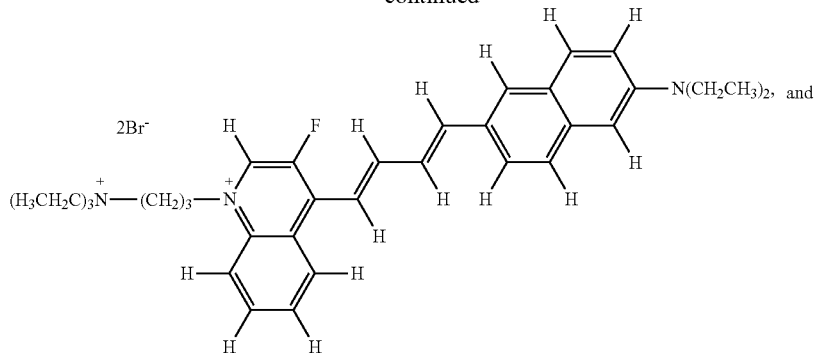
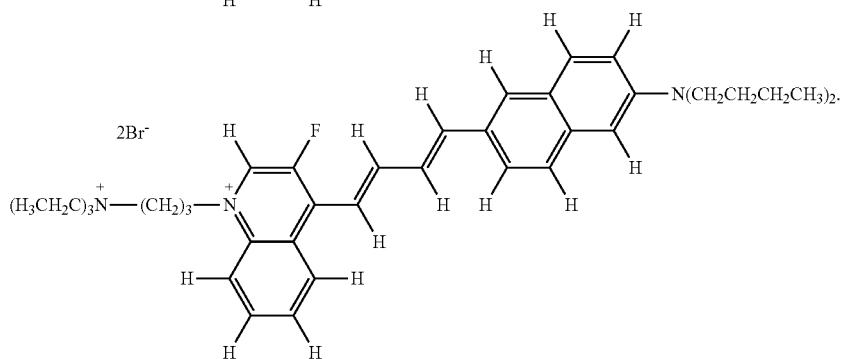
Embodiment 23: The fluorinated voltage sensitive dye of embodiment 1, selected from the group consisting of
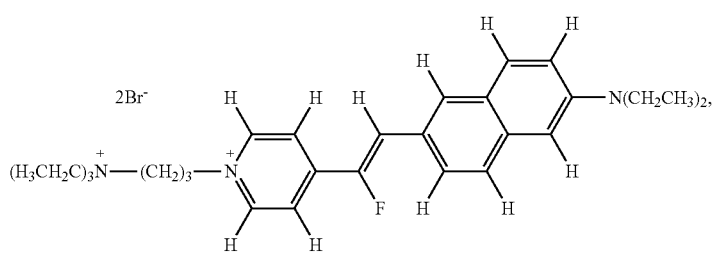
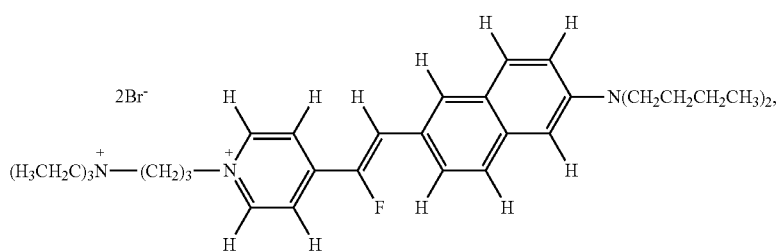
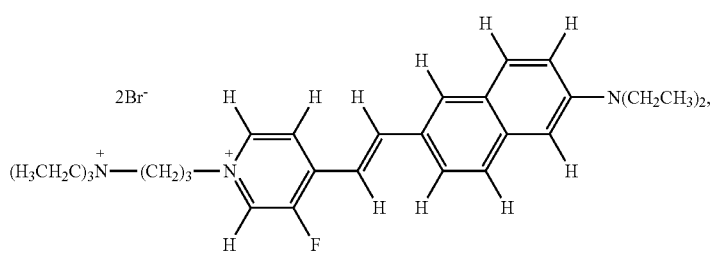

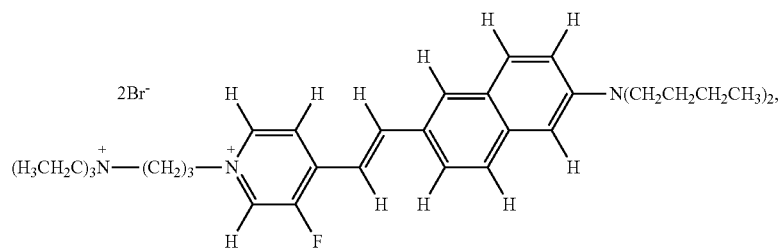
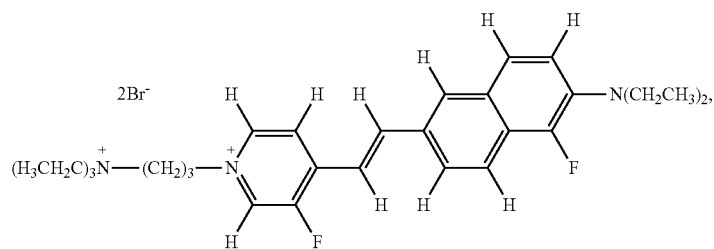
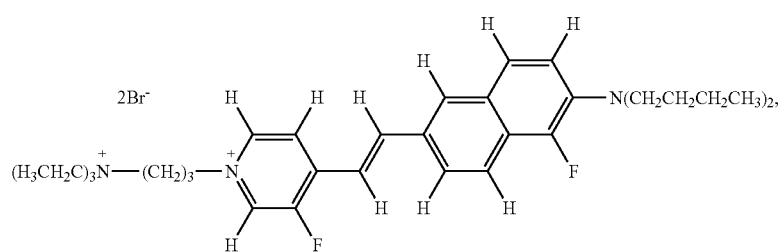
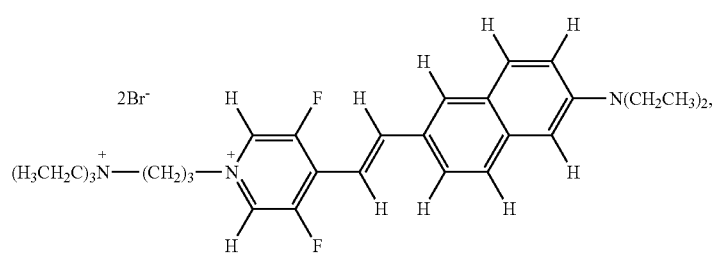
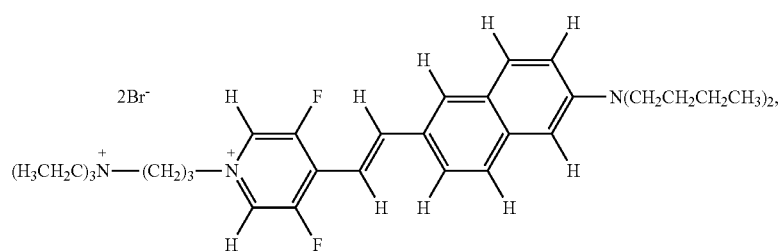
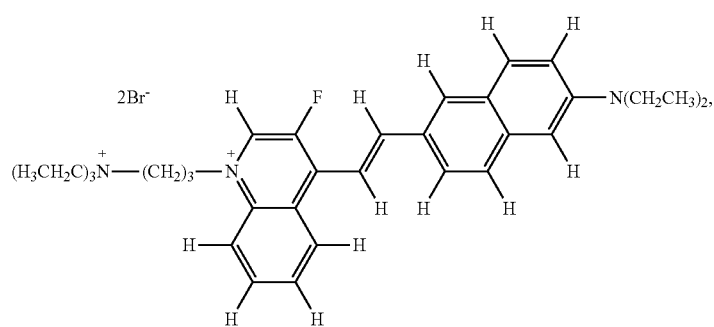

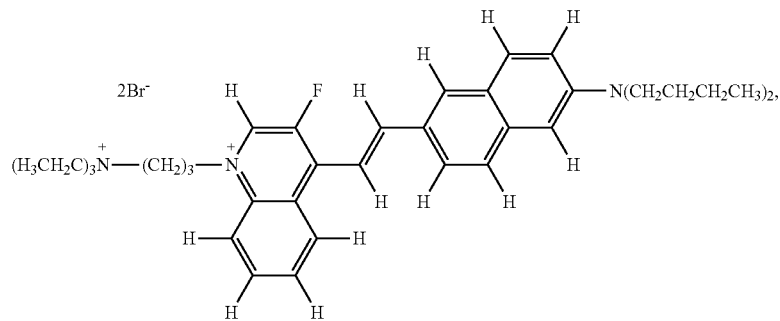
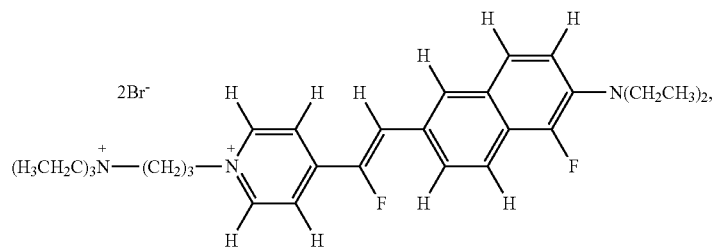
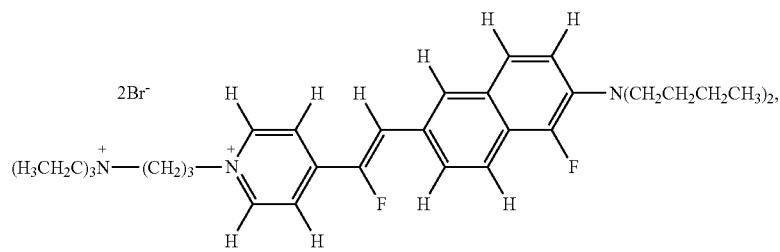
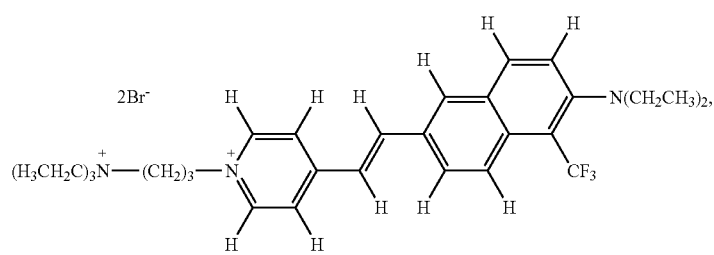
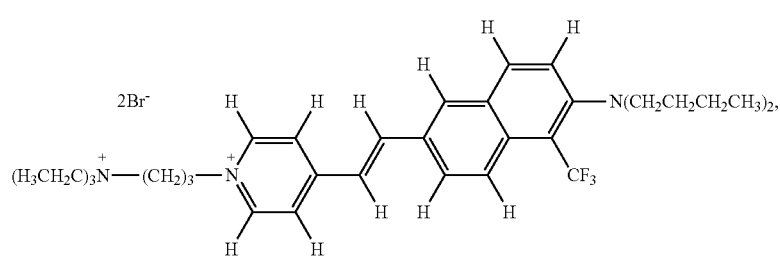
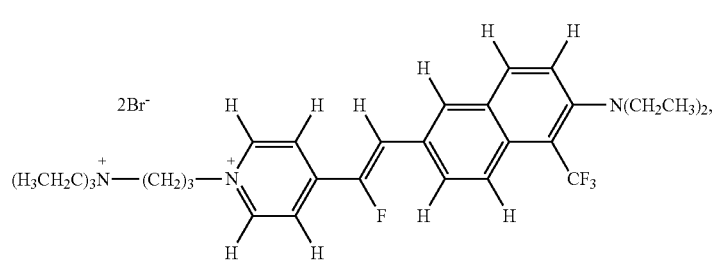

-continued
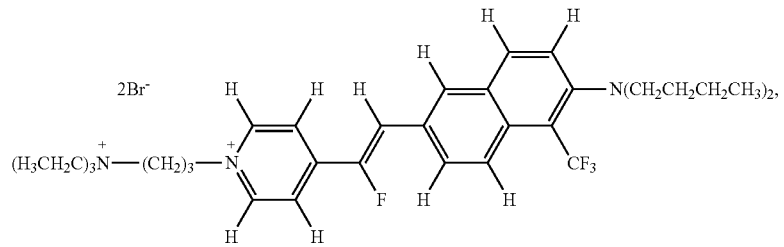
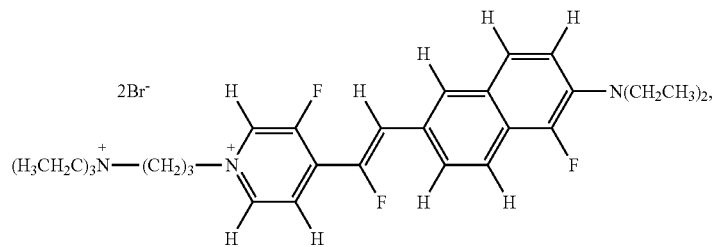
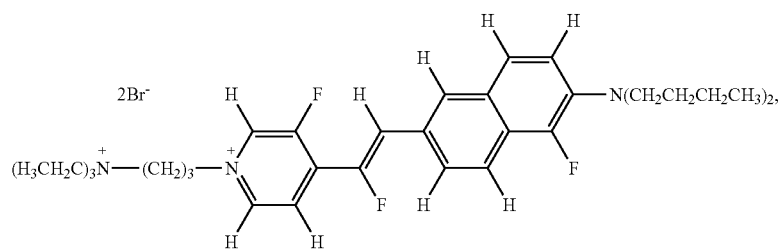
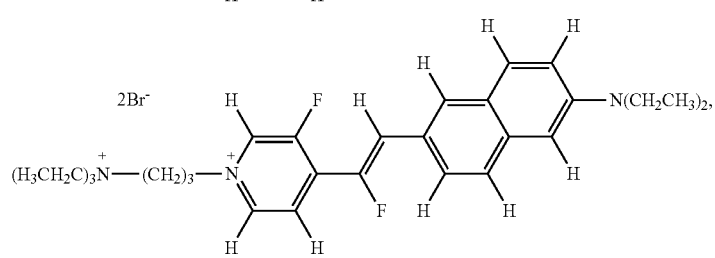
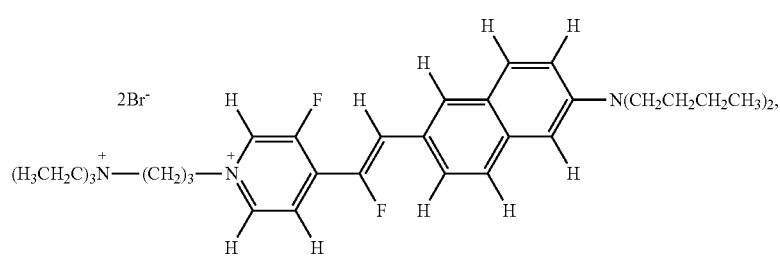
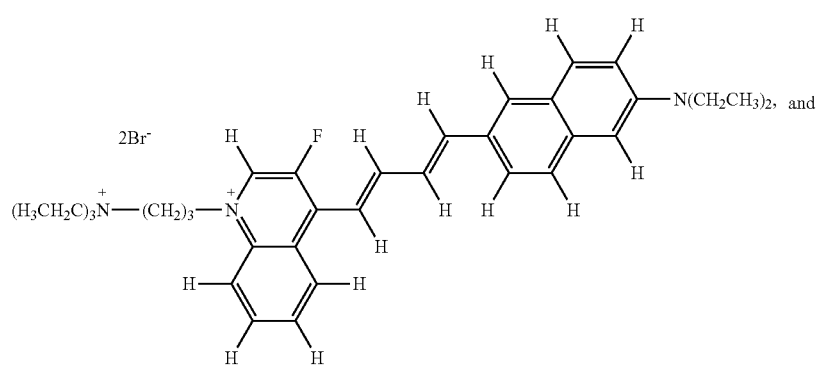

-continued

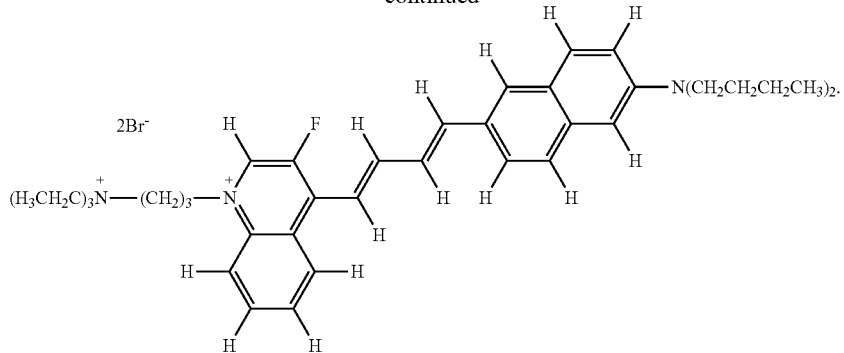

Embodiment 24: A method of forming a fluorinated voltage sensitive dye, the method comprising: reacting a 1-(optionally substituted $C_1$-$C_{12}$ alkyl)-4-methylpyridinium compound and a 6-dialkylaminonaphthalene-2-carboxaldehyde to form the fluorinated voltage sensitive dye; wherein the 1-(optionally substituted $C_1$-$C_{12}$ alkyl)-4-methylpyridinium compound has the structure

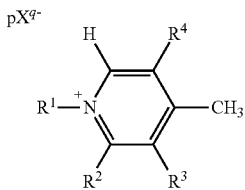

wherein p is 0, 1, or 2; $X^{q-}$ is an anionic counterion having a charge, q, that is 1 or 2; $R^1$ is an optionally substituted $C_1$-$C_{12}$ alkyl; $R^2$ is hydrogen, and $R^3$ is hydrogen or fluorine; or $R^2$ and $R^3$ collectively form a divalent —CH=CH—CH=CH— group; and $R^4$ is hydrogen or fluorine; wherein the 6-dialkylaminonaphthalene-2-carboxaldehyde has the structure

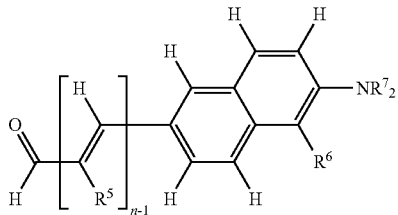

wherein n is 1 or 2; each occurrence of $R^5$ is independently hydrogen or fluorine; $R^6$ is hydrogen or fluorine or trifluoromethyl; and each occurrence of $R^7$ is independently $C_1$-$C_6$ alkyl; and wherein the fluorinated voltage sensitive dye has the structure

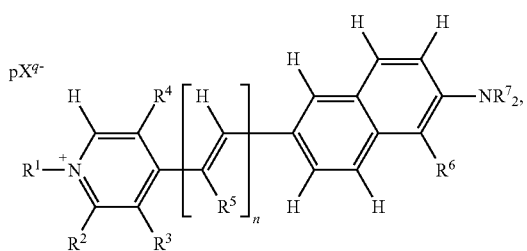

wherein p, $X^{q-}$, n, and $R^1$-$R^7$ are as defined above, and the dye comprises at least one fluorine atom.

Embodiment 25: A method utilizing a fluorinated voltage sensitive dye of embodiment 1 for the optical assessment, monitoring, and/or evaluation of electrophysiology of organelles, cells, or tissues.

Embodiment 26: The method of embodiment 25, wherein the method comprises monitoring a change in wavelength and/or intensity of a fluorescence emission from one-photon excitation or two-photon excitation of the fluorinated voltage sensitive dye.

Embodiment 27: The method of embodiment 25 or 26, wherein the method comprises monitoring the dynamics of action potentials in axons and/or dendrites.

Embodiment 28: The method of embodiment 27, comprising monitoring the dynamics of action potentials in a dendritic spine.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

All ranges disclosed herein are inclusive of the endpoints, and the endpoints are independently combinable with each other. Each range disclosed herein constitutes a disclosure of any point or sub-range lying within the disclosed range.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The invention is further illustrated by the following non-limiting working examples.

Materials and Methods

Synthesis of di-2-AN(F)EPPTEA

General. A chemical scheme for the synthesis of the dye designated di-2-AN(F)EPPTEA is shown in FIG. 1. 6-Diethylamino-naphthalene-2-carboxaldehyde (1) and 1-(3-triethylammoniopropyl)-4-methylpyridinium dibromide (3) were synthesized according to the literature procedures. H. Wang, Z. Lu, S. Lord, K. Willets, J. Bertke, S. Bunge, W. Moerner, and R. Twieg, 2007, "The influence of tetrahydroquinoline rings in dicyanomethylenedihydrofuran (DCDHF) single-molecule fluorophores", *Tetrahedron*, pages 103-114; P. Yan, A. Xie, M. Wei, and L. Loew, 2008, "Amino(oligo)thiophene-based environmentally sensitive biomembrane chromophores", *Journal of Organic Chemistry*, pages 6587-6594. Column chromatography for Di-2-AN(F)EPPTEA was performed on Unibond Amino silica gel from Analtech.

6-Diethylamino-5-fluoro-naphthalene-2-carboxaldehyde (2). N-fluorobenzenesulfonimide (57.0 milligrams, 0.18 millimole) was added to a solution of 6-diethylamino-naphthalene-2-carboxaldehyde (1, 40.0 milligrams, 0.18 millimole) in 5 milliliters of anhydrous N,N-dimethylformamide under argon at −40° C. The mixture was allowed to warm up to room temperature slowly. After 3 hours, 10 milliliters of 10% $K_2CO_3$ aqueous solution was added and the product was extracted with ethyl acetate (3×50 milliliters). Solvent was removed by rotary evaporation and the residue was purified by chromatography ($SiO_2$, 1:1 hexane/$CH_2Cl_2$) to give 2 as yellow needles (35.0 milligrams, 79%). $R_f$ (silica gel, 1:1 Hex/$CH_2Cl_2$)=0.74; $^1$H NMR (400 MHz, $CDCl_3$) δ 1.21 (t, J=7.0 Hz, 6 H), 3.45 (q, J=7.0 Hz, 4 H), 7.25 (t, J=8.8 Hz, 1 H), 7.65 (d, J=8.8 Hz, 1 H), 7.89 (dd, J=1.2 Hz, 8.8 Hz, 1 H), 8.00 (d, J=8.8 Hz, 1 H), 8.19 (s, 1 H), 10.06 (s, 1 H).

Di-2-AN(F)EPPTEA. 6-Diethylamino-5-fluoro-naphthalene-2-carboxaldehyde (2, 16 milligrams, 66 micromoles) and 1-(3-triethylammoniopropyl)-4-methylpyridinium dibromide (3, 26 milligrams, 66 micromoles) were mixed in 2 milliliters of ethanol, and then two drops of pyrrolidine was added. The solution was stirred at room temperature for 16 hours and it turned red after reaction. Solvent was removed by rotary evaporation and the residue was purified by chromatography ($SiO_2$-amino, 5:95 MeOH/$CH_2Cl_2$) to give a red solid (16.4 milligrams, 40%). $R_f$ (silica gel, 24:4:16:6:6 $CHCl_3$/i-PrOH/MeOH/$H_2O$/AcOH)=0.26; $^1$H NMR (400 MHz, $CD_3OD$) δ 1.18 (t, J=7.2 Hz, 6 H), 1.35 (t, J=7.0 Hz, 9 H), 2.50 (m, 2 H), 3.36-3.50 (m, 12 H), 4.68 (t, J=7.6 Hz, 2 H), 7.36 (t, J=8.8 Hz, 1 H), 7.52 (d, J=16.0 Hz, 1 H), 7.67 (d, J=8.8 Hz, 1 H), 7.91 (dd, J=1.2 Hz, 8.8 Hz), 7.98 (d, J=8.8 Hz, 1 H), 8.09 (s, 1 H), 8.12 (d, J=16.0 Hz, 1 H), 8.25 (d, J=6.4 Hz, 2 H), 8.93 (d, J=6.4 Hz, 2 H); HRMS (FAB+): m/z=542.2548 [M-Br]$^+$(calculated for $C_{30}H_{42}BrFN_3^+$: 542.2546).

Additional Dyes

Similar methods were used to prepare additional dyes. Table 1 lists additional dyes and their spectroscopic and electrical properties.

TABLE 1

| Compound | | $\lambda_{max}^{abs}$ (nm); log ε | $\lambda_{max}^{em}$ (nm); FQY | Photo-bleaching rate [e] (Relative to unsubstituted dye) | Voltage sensitivity [f] ΔF/F per 100 mV Ex/Em (nm) |
|---|---|---|---|---|---|
| PY3006 | | 539; 4.5 [a]<br>493; 4.2 [b]<br>488; 4.4 [c] | 720; 0.001 [a]<br>— [d]<br>636; 0.16 [c] | 0.63 | 12%<br>578/<br>>695 |
| PY3128 | | 545; 4.4 [a]<br>506; 4.2 [b]<br>495; 4.3 [c] | 720; 0.002 [a]<br>— [d]<br>632; 0.26 [c] | 0.63 | 6%<br>590/<br>>695 |
| PY3174 | | 481; 4.4 [a]<br>401; 4.2 [b]<br>444; 4.3 [c] | 704; 0.007 [a]<br>666; 0.002 [d]<br>610; 0.25 [c] | 0.83 | 6%<br>545/<br>>695 |

TABLE 1-continued
| Compound | $\lambda_{max}^{abs}$ (nm); log ε | $\lambda_{max}^{em}$ (nm); FQY | Photo-bleaching rate[e] (Relative to unsubstituted dye) | Voltage sensitivity[f] ΔF/F per 100 mV Ex/Em (nm) |
|---|---|---|---|---|
| PY3179 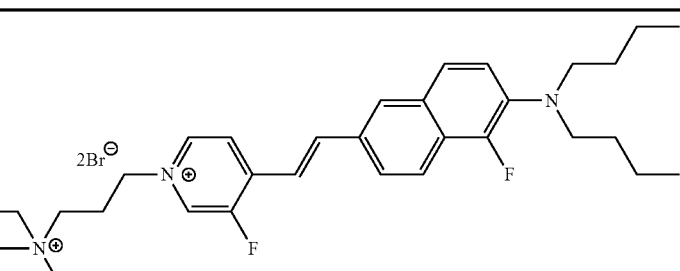 | 509; 4.3[a]<br>414; 4.1[b]<br>465; 4.3[c] | 720; 0.003[a]<br>—[d]<br>632; 0.22[c] | 0.91 | 18%<br>572/<br>>695 |
| PY3184 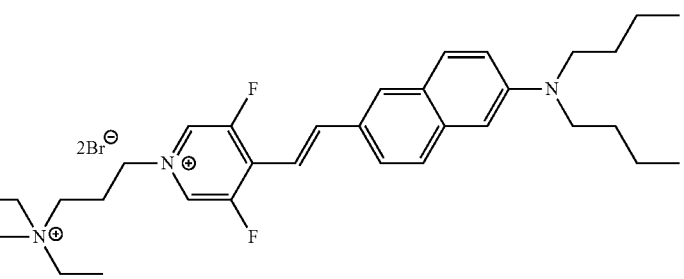 | 569; 4.6[a]<br>530; 4.2[b]<br>511; 4.3[c] | 658; 0.004[a]<br>—[d]<br>646; 0.18[c] | 1.56 | 11%<br>610/<br>>695 |
| PY3304 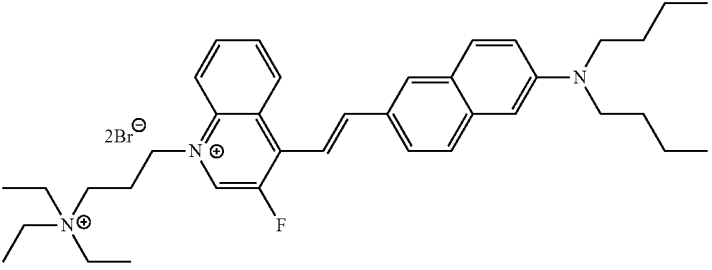 | 617; 4.4[a]<br>565; 4.0[b]<br>547; 4.2[c] | 825; 0.001[a]<br>—[d]<br>686; 0.03[c] | 5.26 | 12%<br>645/<br>>745 |
| PY4038 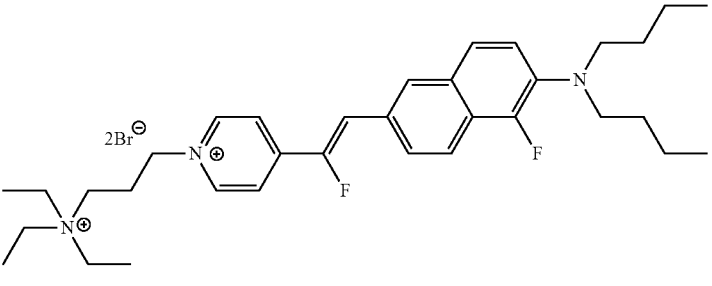 | 497; 4.4[a]<br>409; 4.0[b]<br>464; 4.3[c] | 760; 0.001[a]<br>—[d]<br>643; 0.26[c] | 0.62 | 7%<br>578/<br>>695 |
| PY4093 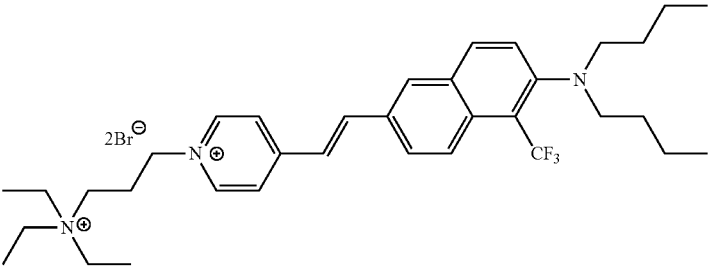 | 449; 4.6[a]<br>430; 4.3[b]<br>418; 4.5[c] | 687; 0.046[a]<br>7.15:0.005[b]<br>597; 0.35[c] | 0.95 | 8%<br>530/<br>>645 |

TABLE 1-continued

| Compound | $\lambda_{max}^{abs}$ (nm); log ε | $\lambda_{max}^{em}$ (nm); FQY | Photobleaching rate[e] (Relative to unsubstituted dye) | Voltage sensitivity[f] ΔF/F per 100 mV Ex/Em (nm) |
|---|---|---|---|---|
| PY4125 | 453; 4.4[a]<br>395; 4.2[b]<br>422; 4.4[c] | 694; 0.006[a]<br>624; 0.004[b]<br>590; 0.30[c] | 1.35 | 5%<br>510/<br>>695 |
| PY4158 | 510; 4.3[a]<br>408; 4.0[b]<br>470; 4.2[c] | 845; 0.003[a]<br>—[d]<br>651; 0.23[c] | 0.89 | 7%<br>580/<br>>695 |
| PY4160 | 558; 4.6[a]<br>513; 4.4[b]<br>500; 4.5[c] | 710; 0.003[a]<br>—[d]<br>660; 0.21[c] | 0.66 | 10%<br>602/<br>>695 |
| PY4221 | 627; 4.4[a]<br>537; 4.1[b]<br>553; 4.2[c] | —[d]<br>—[d]<br>743; 0.07[c] |  | 6%<br>670/<br>>780 |

[a] Ethanol.
[b] PBS buffer.
[c] Lipid vesicles.
[d] FQY < 0.001.
[e] Photobleaching rates were measured by single exponential decay fitting of the absorbance of dyes irradiated with white light from a xenon lamp.
[f] Fluorescence changes for a 100 millivolt step in membrane potential were measured with excitation through a monochromator (20 nanometer bandwidth) and emission through a long pass filter at the indicated wavelengths.

Single-voxel, 2-photon Recordings

To record from individual spines, a spot recording technique was used (M. Nuriya, J. Jiang, B. Nemet, K. Eisenthal, and R. Yuste, 2006, "Imaging membrane potential in dendritic spines", *Proceedings of the National Academy of Sciences of the United States of America*, pages 786-790). The spot recording technique was synchronized to the electrical stimulation with sampling at 10 kilohertz. Because 2-photon excitation restricts the extent of excitation in the vertical dimension, we term this "single-voxel" recording. ScanImage, (MATLAB based, 2) was used to acquire images of regions with visible spines. Pixel times for frames were typically 3.2 microseconds and PMT signals were low-pass filtered with a filter cutoff of 300 kilohertz. Custom software was written (VoxelRecordVSD.m,) to select targets from these frames, position the laser at the selected location, and record PMT signals for a given duration (typically 40-60 milliseconds). While recording from single voxels, the software automatically switched the low-pass filter cutoff from 300 kilohertz to 3 kilohertz (serial communication with Stanford Research SR570). Signals were sampled at 1 megahertz and decimated (downsampled) twice by a factor of 10 to reduce the sampling to 10 kilohertz. Additional 3 kilohertz filtering was built into the decimation software, and "zero-phase" filtering (filtfilt, MATLAB) was used to preserve signal timing, allowing accurate measurement of propagation delays of back-propagating action potentials traveling from soma to dendrite. Control data were first high pass filtered at 100 hertz before taking the standard deviation when computing signal-to-noise.

Custom 2-photon Microscope and Optics

A Zeiss AxioSkop 2FS MOT was modified for 2-photon excitation as follows. A 40×1.0NA water objective (Zeiss, W Plan-Apochromat 1.0) was used for excitation. A transfluorescence light path was added using a 1.2NA water immersion condenser (Zeiss) coupled to a photomultiplier tube (PMT). PMTs were Hamamatsu GaAs(P) (H10770PA-40). The Ti:Sapphire laser was a Coherent Chameleon Ultra II, with an electro-optic modulator (Conoptics Model 350-80LA with BK option), and scanning was performed with Cambridge Technology galvanometers (6215(y) and 6215H(x)). Excitation and epifluorescence light was separated by a 735 nanometer long-pass dichroic (Semrock FF01 735-Di01) and 640/120 nanometer emission filters were used (Chroma HQ 640/120 M 2P).

Brain Slice Electrophysiology

Acute brain slices were prepared from p24-p28 CD1 mice as described previously (C. D. Acker and S. D. Antic, 2009, "Quantitative assessment of the distributions of membrane conductances involved in action potential backpropagation along basal dendrites", *Journal of Neurophysiology*, volume 101, pages 1524-1541). Intracellular solution contained (in millimolar units) 135 K-gluconate, 2 $MgCl_2$, 2 Mg-ATP, 10 Na-phosphocreatine, 0.3 Na-GTP, 10 HEPES, and 0.01 EGTA (pH 7.4, adjusted with KOH). ACSF contained (in millimolar units) 127 NaCl, 25 $NaHCO_3$, 25 D-glucose, 2.5 KCl, 1.25 $NaH_2PO_4$, 2 $CaCl_2$, and 1 $MgCl_2$ (pH 7.3). All recordings done at room temperature.

Dye Loading and Visualization of Dendritic Arbor

Using previously established techniques for loading similar voltage-sensitive dyes into neurons via a somatic whole-cell patch pipette, we were able to visualize apical dendritic trees of cortical pyramidal neurons in brain slice preparations with di-2-AN(F)EPPTEA. As previously described, "repatching" was necessary to allow the dye to diffuse sufficiently to distal dendritic regions (S. D. Antic, 2003, "Action potentials in basal and oblique dendrites of rat neocortical pyramidal neurons", *Journal of Physiology-London*, volume 550, pages 35-50). For the neuron shown in FIG. 2A, dye was allowed to diffuse for 35 minutes before repatching the neuron with a dye-free pipette.

Experimental Results

Figure 2:
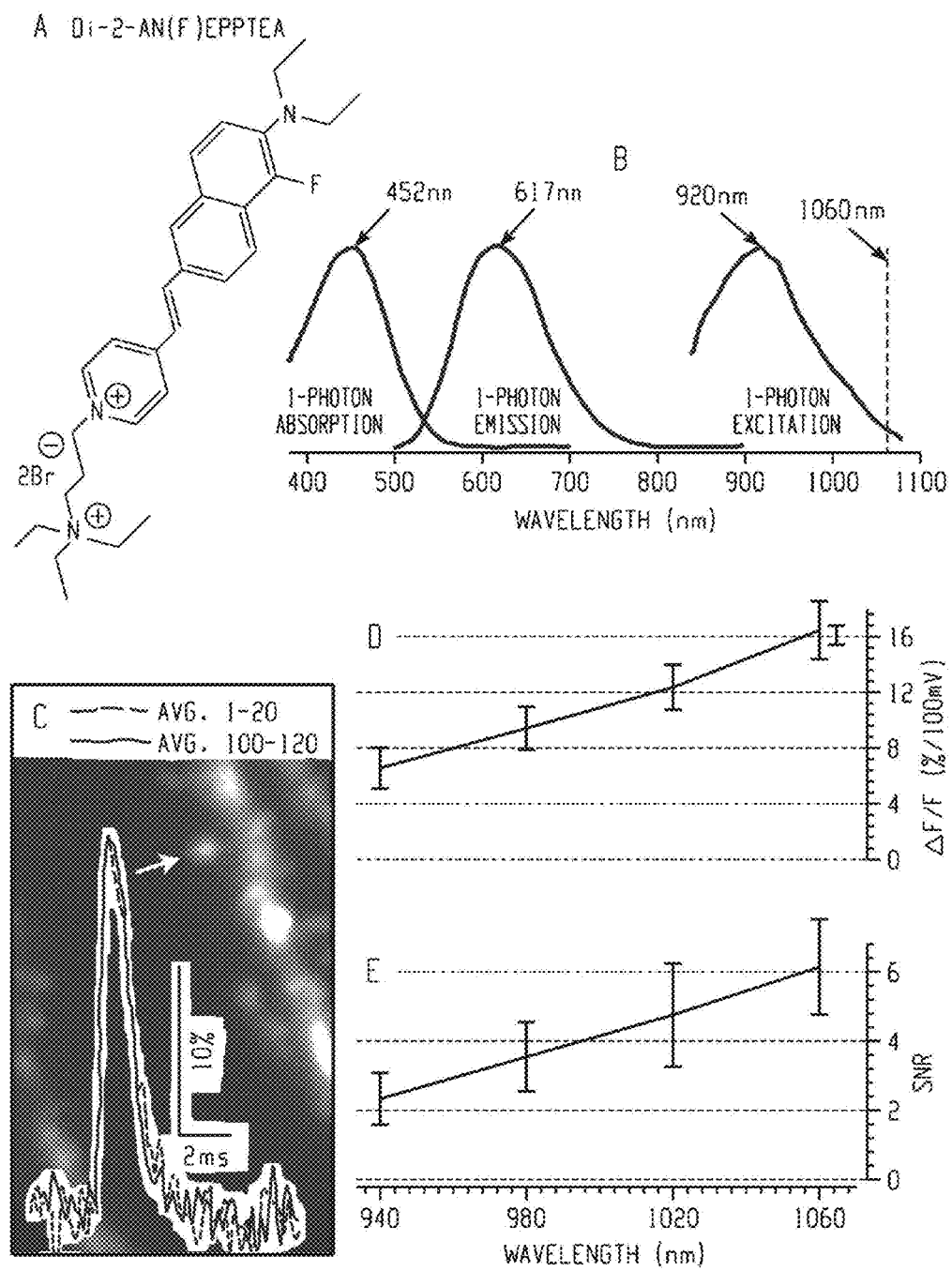
FIG. 2 generally relates to the stability and voltage-sensitivity of di-2-AN(F)EPPTEA; 2A is the chemical structure of di-2-AN(F)EPPTEA; 2B includes the one-photon absorption, one-photon emission, and two-photon excitation spectra of di-2-AN(F)EPPTEA; 2C shows overlapped averages of first and last 20 (of 100) recordings of back-propagating action potentials in a single spine, with no change in signal; 2D is a plot of two-photon voltage sensitivity as a function of excitation wavelength, measured using bAP amplitudes at proximal splines, normalized by somatic AP amplitude (100 millivolts somatic); for each of N=9 spines (5 cells), all four wavelengths were tested (error bars are standard deviations); the gray point in the upper right of the plot includes other proximal spines measured at 1060 nanometers (16.1%, N=15 spines, 7 cells, error bar is the standard error of the mean; 2E is a plot of "single sweep" signal-to-noise ratios (SNRs); SNR values are normalized by the square root of the number of sweeps.

These experiments utilized the dye designated di-2-AN(F) EPPTEA, the structure of which is shown in FIG. 2A. The 2-photon excitation spectrum of di-2-AN(F)EPPTEA was measured by tuning the Ti-Sapphire laser in 20 nanometer increments and finding a peak excitation wavelength of 920 nanometers (FIG. 2B). To maximize sensitivity in VSD imaging of this class of hemicyanine dyes, it is necessary to select excitation wavelengths significantly longer than the peak (so called "red-edge excitation") (L. M. Loew, 1982, "Design and characterization of electrochromic membrane probes", *Journal of Biochemical and Biophysical Methods*, volume 6, pages 243-260; B. Kuhn, P. Fromherz, and W. Denk, 2004, "High sensitivity of stark-shift voltage-sensing dyes by one- or two-photon excitation near the red spectral edge", *Biophysical Journal*, volume 87, pages 631-639). For di-2-AN (F)EPPTEA, voltage-sensitivity rises nearly linearly with increasing 2-photon excitation wavelength (FIG. 2D). This was established by repeating recordings of back-propagating action potentials (bAPs) in single spines and varying excitation wavelength from 940 to 1060 nanometers. Laser power was adjusted (increased with increasing wavelength) to match baseline signal levels for a fair comparison of signal-to-noise, which also increased with wavelength (FIG. 2E). At 1060 nanometers, the voltage-sensitivity in the spine was determined to be 16.1% per 100 millivolt change at the soma. These recordings were performed at the most proximal visible spines on basal dendrites (<30 micrometers). Because there may be a small decrement in the bAP amplitude at the proximal dendrites (S. D. Antic, 2003, "Action potentials in basal and oblique dendrites of rat neocortical pyramidal neurons", *The Journal of Physiology (London)*, volume 550, pages 35-50), this may slightly underestimate the actual voltage sensitivity. We saw no signs of photodamage or toxicity, even when recording over 100 sweeps from individual spines at 1060 nanometers (FIG. 2C).

Figure 3:
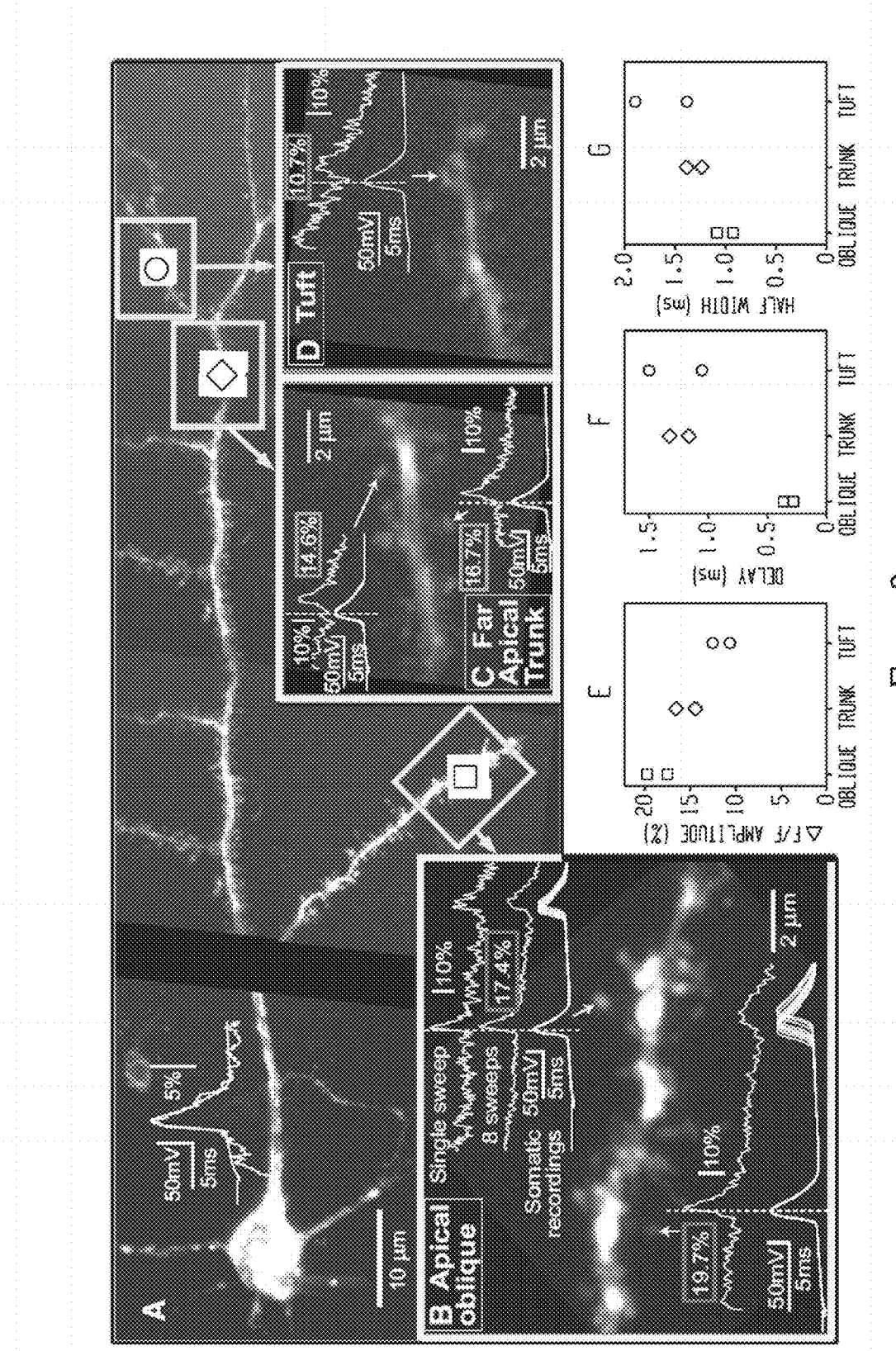
FIG. 3 generally relates to imaging of action potential back-propagation and invasion of dendritic spines using di-2-AN(F)EPPTEA; 3A is an image montage of a layer V pyramidal neuron loaded via somatic patch pipette with di-2-AN(F)EPPTEA; the traces at the upper left show superimposed somatic electrical and perisomatic dye records, both at 10 kilohertz, demonstrating precise temporal synchronization; 3B is another montage including recordings of back-propagating action potentials (bAPs, 2 spikes, analysis applies to first spike only), elicited using somatic current injection, at two different spines in the same region on an apical oblique dendrite; somatic electrical waveforms with multiple recordings aligned at the first spike are shown below single-voxel imaging data from spines; inset boxes show the amplitudes of the optically recorded bAP waveforms; for the top spine, a single optical sweep is shown along with the average of 8 temporally aligned sweeps; single sweep measurements: 18.0% amplitude, 0.29 millisecond delay, 0.32 millisecond rise time, 0.83 millisecond half-width, SNR=8.3); 3C is the same as 3B, except two spines are targeted on a distal apical trunk region; 3D is a dye recording from a spine on the apical tuft; 3E, 3F, and 3G are summaries of amplitudes, propagation delay times (optical relative to electrical peak time), and half-widths for bAPs recorded in spines in all three regions; in all cases, spines (indicated by arrows) were placed in focus and targeted at their centers; vertical dashed lines indicate peak times of somatic action potentials.

Single-voxel recordings at 10 kilohertz triggered by electrophysiology were performed to track backpropagating action potentials in individual spines at different regions along the dendritic tree. Dye was loaded internally via the somatic whole cell patch electrode. The dye-filled pipette was removed and the cell was repatched with a dye-free pipette after a period of 35 minutes (G. Stuart, N. Spruston, B. Sakmann, and M. Häusser, 1997, "Action potential initiation and back-propagation in neurons of the mammalian CNS", *Trends in Neurosciences*, volume 20, pages 125-131), a procedure that provided adequate staining of the dendritic arbor (FIG. 3A). Action potentials (APs) were elicited by somatic current injection via the patch electrode. At the most proximal recording location (an apical oblique dendrite, about 65 micrometer path distance from the center of the cell body, ignoring small scale curvature and changes in depth), the physiology of two different spines (inter-spine distance about 8 micrometers) were explored using single-voxel 2-photon VSD imaging (FIG. 3B). In spite of significantly different baseline intensities (bottom targeted spine, 35% as bright as top spine, presumably due to different spine sizes or membrane areas) the measured ΔF/F amplitudes were similar, 17.4 and 19.7%. Recordings from the larger spine produced good quality waveforms in single sweeps (signal-to-noise ratio, SNR=8.3 for single sweep, FIG. 3B). The average of 8 sweeps, temporally aligned to the peak of the first AP in the electrical recording, produced a SNR of 27.7.

Two spines at a distal region along the apical trunk yielded ΔF/F amplitudes of 16.7, and 14.6% (FIG. 3C). Again, the amplitudes seen at two separate spines in the same region were similar However, they were significantly smaller than the amplitudes observed at the apical oblique recording site. Finally, at a distal recording location in the apical tuft, signals were clearly diminished (FIG. 3D); while the distance to this tuft region is not much further from the soma than in FIG. 3C, the caliber of the tuft dendrite is smaller than the trunk. Signal amplitudes from all spines recorded are given in FIG. 3E. The simplest explanation for the observed consistency between fluorescence changes in pairs of spines within local dendritic regions is that: (1) the attenuation of the bAP with distance is gradual (G. J. Stuart and B. Sakmann, 1994, "Active propagation of somatic action potentials into neocortical pyramidal cell dendrites", *Nature*, volume 367, pages 69-72) such that the parent dendritic segments for the different spines see approximately the same bAP amplitude; (2) bAPs invade different spines with little or no attenuation (M. Nuriya, J. Jiang, B. Nemet, K. Eisenthal, and R. Yuste, 2006, "Imaging membrane potential in dendritic spines", *Proceedings of the National Academy of Sciences of the United States of America*, pages 786-790; L. M. Palmer and G. J. Stuart, 2009, "Membrane Potential Changes in Dendritic Spines during Action Potentials and Synaptic Input", *The Journal of Neuroscience*, volume 29, pages 6897-6903; K. Holthoff, D. Zecevic, and A. Konnerth, 2010, "Rapid time course of action potentials in spines and remote dendrites of mouse visual cortex neurons", *The Journal of Physiology (London)*, volume 588, pages 1085-1096), also see FIG. 4, described below; (3) the sensitivity of the VSD recordings from spines is not significantly corrupted by differences in spine size, or differences in internally bound dye (contributing to background fluorescence).

As with the bAP amplitude, propagation delays were also consistent between spines in the same region with more proximal regions showing 0.3 millisecond delays, while the most distal spines showed 1.1 and 1.5 millisecond delays (FIG. 3F). These delays, measured in spines, are readily resolved because of our high time resolution, which is enabled by the excellent signal-to-noise of these recordings, and are consistent with measurements of bAP delays in the dendrite, measured either electrically (G. J. Stuart, and B. Sakmann, 1994, "Active propagation of somatic action potentials into neocortical pyramidal cell dendrites", *Nature*, volume 367, pages 69-72) or optically (W. L. Zhou, P. Yan, J. P. Wuskell, L. M. Loew, and S. D. Antic, 2008, "Dynamics of action potential back-propagation in basal dendrites of prefrontal cortical pyramidal neurons", *European Journal of Neuroscience*, volume 27, pages 923-936). Our recordings from spines also indicate that back-propagation is decremental in the present example, a conclusion that is consistent with the observed changes in waveform shape across dendritic regions. In particular, half-widths increase from an average of 1.0 to 1.7 milliseconds from the more proximal apical oblique region to the more distal apical tuft region (FIG. 3G).

Figure 4:
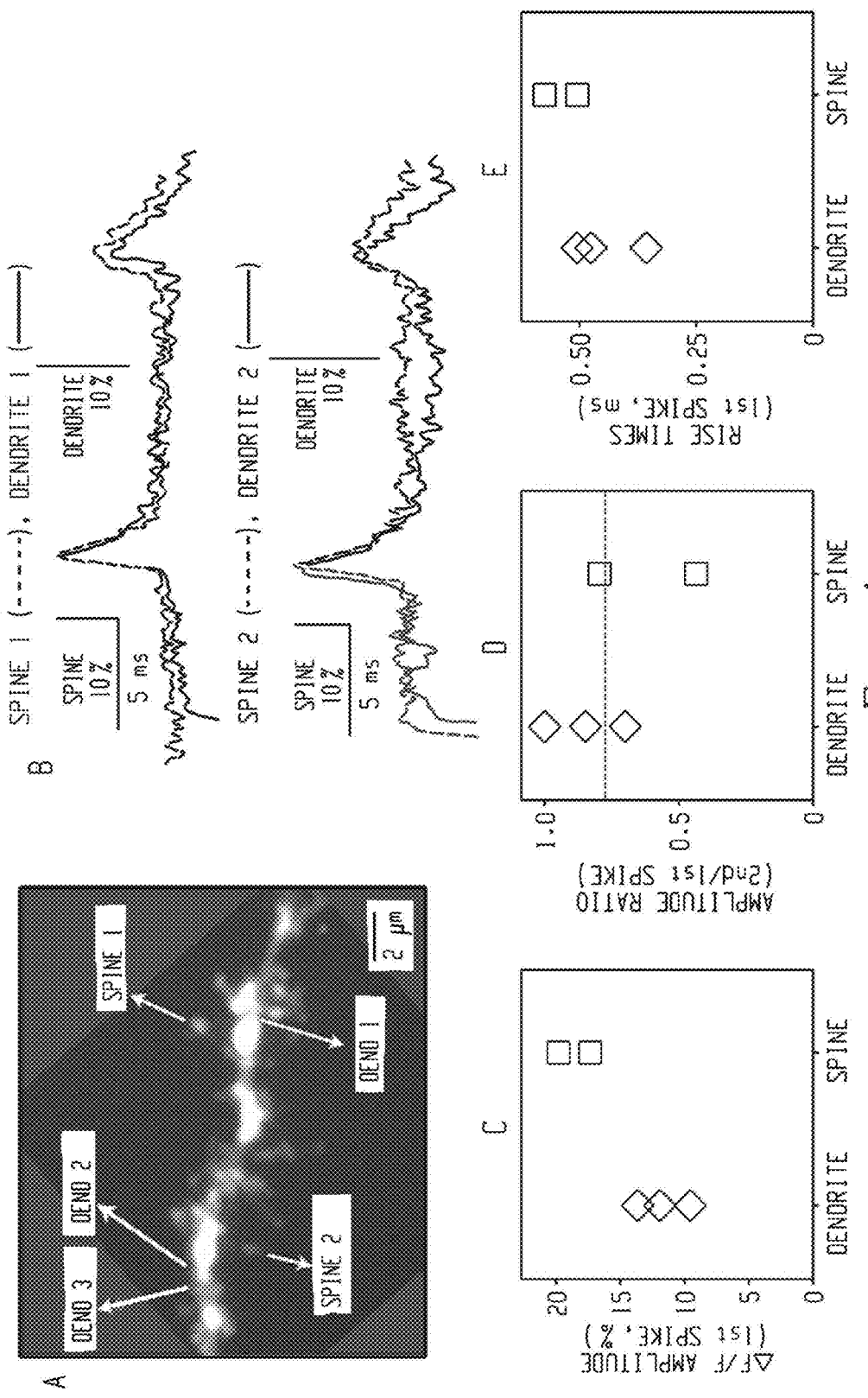
FIG. 4 generally relates to bAP waveforms in spines and their parent dendrites; 4A shows an apical oblique dendrite region (same as FIG. 3B) with 2 spine and 3 dendrite recording sites labeled; 4B shows superimposed recordings from spines (gray) and parent dendrite (black); note different vertical scale bar for spines and dendrites; somatic current injection generates 2 spikes, waveforms are averages (8-10 sweeps) aligned by first spike; 4C is a plot of amplitudes of optically recorded bAPs (first spikes only); 4D is a plot of the ratio of second spike amplitudes over first, with the somatic value shown by the dashed line at 0.77; 4E is a plot of rise times of all first spikes.

Recordings from parent dendrites near the spines confirmed the results of Holthoff, Zecevic, and Konnerth (2010), showing nearly identical waveforms in spine and parent dendrite (FIG. 4). This effect persisted in spite of significantly narrower bAPs in the apical oblique dendrite than recorded previously in apical dendrites, with rise times of approximately 0.5 milliseconds (FIG. 4E) and widths of approximately 1.0 millisecond (FIG. 3G, Oblique). These results lend further support to the conclusion that bAPs fully invade spines from the adjacent dendrite. Interestingly, parent dendrites typically produced reduced signal amplitudes, with approximately two thirds the amplitude recorded in the spine (in % ΔF/F, FIG. 4C). This is most likely due to the bright internal staining of dendrites compared to spines, which adds background to the measurements.

Since recording bAPs at single spines did not produce noticeable signs of phototoxicity such as changes in action potential shape (FIG. 2C) we developed a more extreme protocol targeted to the soma rather than spines. We rapidly and repeatedly scanned the soma (~1 second/scan) with increasingly intense excitation light and looked for changes in action potential shape. 920 nanometers was used rather than 1060 nanometers, which leads to approximately 10 times more excitation of the dye (FIG. 2B). The changes in somatic action potential shape typically included an about 30% increase in action potential half width, about 15 millivolts depolarization in resting membrane potential, and an about 15 millivolt decrease in peak action potential amplitude. These changes developed gradually over about 100 exposures. Detectors were off during these measurements to prevent saturation or possible damage. Typically, 10-20 milliwatts of average power at 920 nanometers was necessary to cause the above described changes. Further quantification is not feasible however, since the necessary laser power was clearly dependent on the depth of the cell in the slice (laser powers are accurate above slice only), with the deepest cell developing less noticeable changes with even higher powers.

Additional experimental details can be found in C. D. Acker, P. Yan, and L. M. Loew, "Single-Voxel Recording of Voltage Transients in Dendritic Spines", 2011, *Biophysical Journal*, volume 101, pages L11-L13.

To summarize, these experiments demonstrate the use of fluorinated voltage sensitive dyes in a brain slice optical recording method that are optimized for 2-photon measurements of electrical activity in single spines with high spatial and temporal resolution. Decremental propagation of the action potential into spines at remote regions of the dendritic arbor is demonstrated. These results are also consistent with the conclusion of others that back-propagating action potentials invade spines from the adjacent dendrite.

The invention claimed is:
1. A fluorinated voltage sensitive dye having the structure

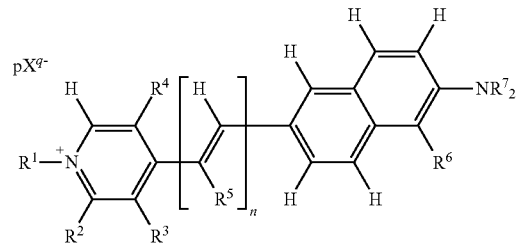

wherein
p is 0, 1, or 2; $X^{q-}$ is an anionic counterion having a charge, q, that is 1 or 2;
n is 1 or 2;
$R^1$ is an optionally substituted $C_1$-$C_{12}$ alkyl;
$R^2$ is hydrogen, and $R^3$ is hydrogen or fluorine; or $R^2$ and $R^3$ collectively form a divalent —CH=CH—CH=CH— group;
$R^4$ and each occurrence of $R^5$ are each independently hydrogen or fluorine;
$R^6$ is hydrogen or fluorine or trifluoromethyl; and
each occurrence of $R^7$ is independently $C_1$-$C_6$ alkyl;
provided that at least one of $R^3$, $R^4$ or $R^6$ is fluorine, or at least one occurrence of $R^5$ is fluorine.

2. The fluorinated voltage sensitive dye of claim 1, wherein $X^{q-}$ is Br$^-$.

3. The fluorinated voltage sensitive dye of claim 1, wherein n is 2, and each occurrence of $R^5$ is hydrogen.

4. The fluorinated voltage sensitive dye of claim 1, wherein n is 1.

5. The fluorinated voltage sensitive dye of claim 1, wherein n is 2.

6. The fluorinated voltage sensitive dye of claim 1, wherein $R^1$ is selected from the group consisting of —CH$_2$CH(OH) CH$_2$N$^+$(CH$_3$)$_2$(CH$_2$CH$_2$OH), —(CH$_2$)$_3$SO$_3^-$, —(CH$_2$)$_4$SO$_3^-$, —(CH$_2$)$_3$—N$^+$(R$^8$)$_3$ wherein each occurrence of $R^8$ is independently $C_1$-$C_6$ alkyl, and —$(CH_2)_2$—$N^+$$(R^9)_3$ wherein each occurrence of $R^9$ is independently $C_1$-$C_6$ alkyl.

7. The fluorinated voltage sensitive dye of claim 1, wherein $R^1$ is —$(CH_2)_3$—$N^+(R^8)_3$ wherein each occurrence of $R^8$ is independently $C_1$-$C_6$ alkyl.

8. The fluorinated voltage sensitive dye of claim 1, wherein $R^2$ and $R^3$ are hydrogen.

9. The fluorinated voltage sensitive dye of claim 1, wherein $R^2$ is hydrogen and $R^3$ is fluorine.

10. The fluorinated voltage sensitive dye of claim 1, wherein $R^2$ and $R^3$ collectively form a divalent —CH=CH—CH=CH— group.

11. The fluorinated voltage sensitive dye of claim 1, wherein $R^4$ is hydrogen.

12. The fluorinated voltage sensitive dye of claim 1, wherein n is 1, and $R^5$ is hydrogen.

13. The fluorinated voltage sensitive dye of claim 1, wherein n is 1, and $R^5$ is fluorine.

14. The fluorinated voltage sensitive dye of claim 1, wherein n is 2, and one occurrence of $R^5$ is hydrogen and the other occurrence of $R^5$ is fluorine.

15. The fluorinated voltage sensitive dye of claim 1, wherein each occurrence of $R^7$ is ethyl, or each occurrence of $R^7$ is n-butyl.

16. The fluorinated voltage sensitive dye of claim 1, wherein the dye comprises no more than four fluorine atoms.

17. The fluorinated voltage sensitive dye of claim 1, wherein the dye comprises four fluorine atoms.

18. The fluorinated voltage sensitive dye of claim 1, wherein the dye comprises three fluorine atoms.

19. The fluorinated voltage sensitive dye of claim 1, wherein the dye comprises two fluorine atoms.

20. The fluorinated voltage sensitive dye of claim 1, wherein the dye comprises one fluorine atom.

21. The fluorinated voltage sensitive dye of claim 1, wherein
$pX^{q-}$ is $2Br^-$;
n is 1;
$R^1$ is —$(CH_2)_3$—$N^+(CH_2CH_3)_3$;
$R^2$, $R^3$, $R^4$, and $R^5$ are hydrogen;
$R^6$ is fluorine; and
each occurrence of $R^7$ is ethyl, or each occurrence of $R^7$ is n-butyl.

22. The fluorinated voltage sensitive dye of claim 1, selected from the group consisting of

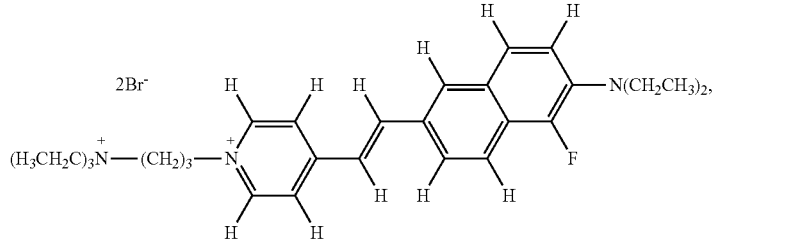

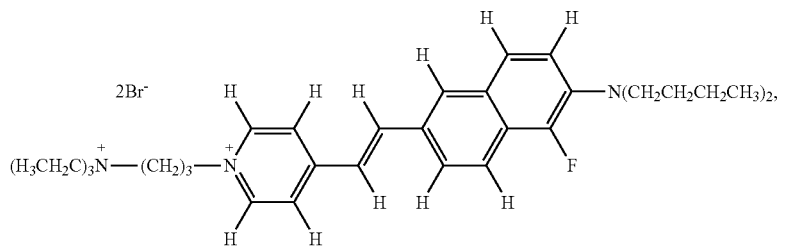

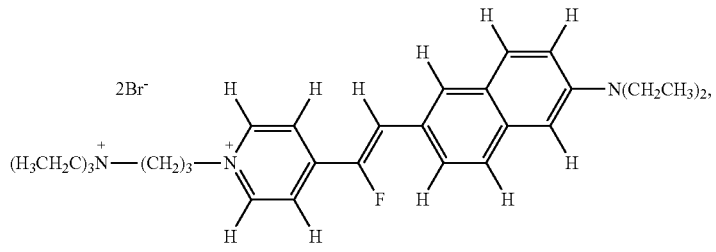

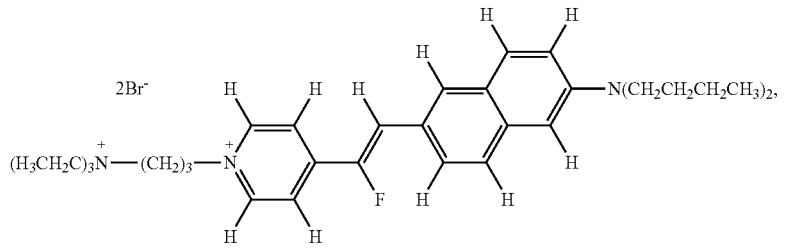

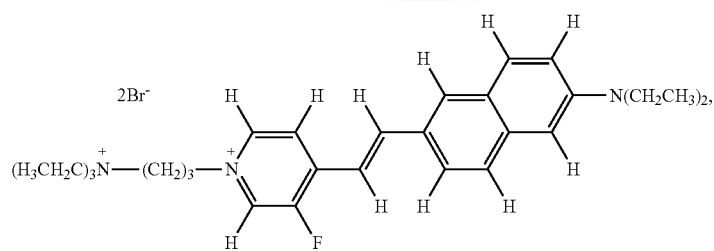
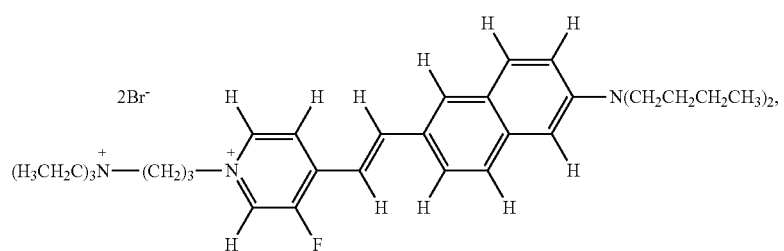
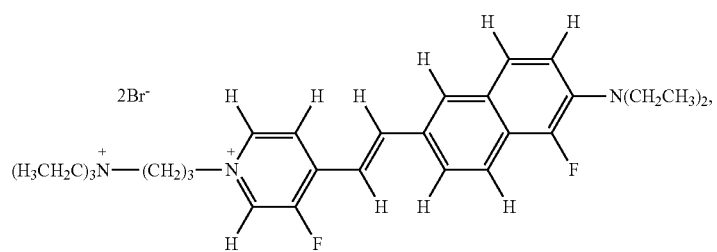
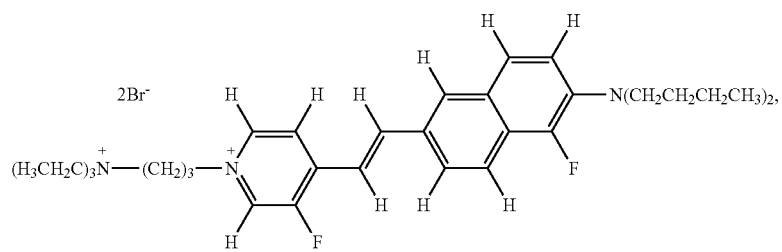
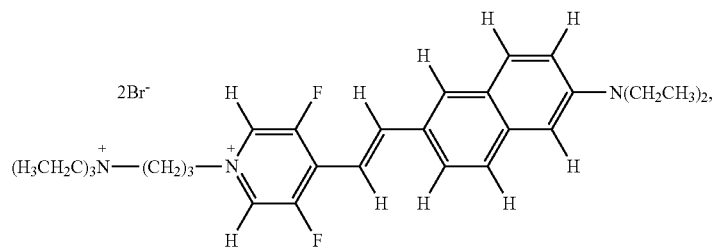
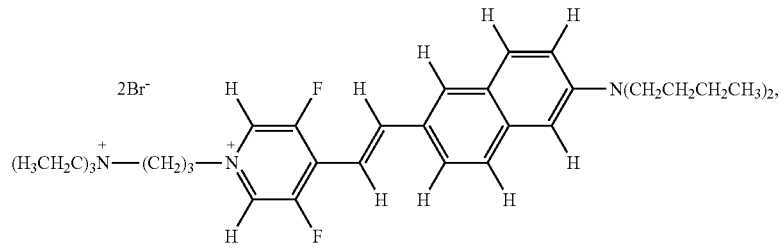

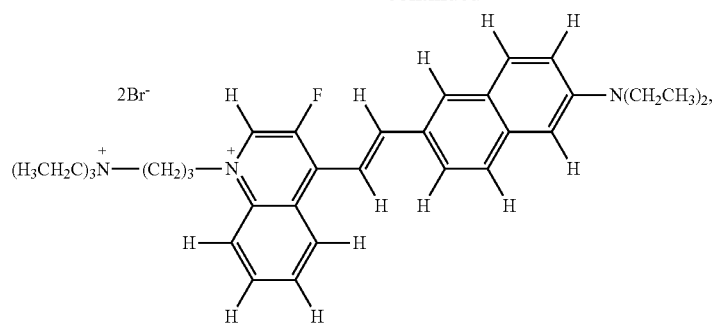
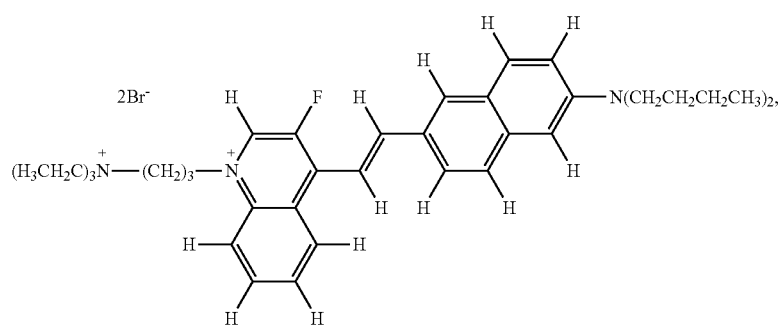
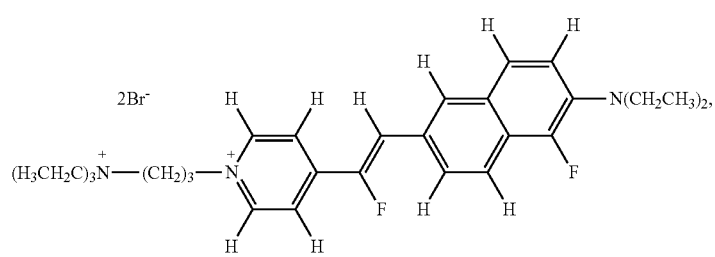
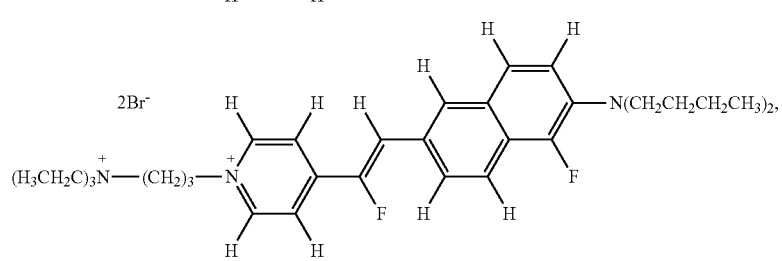
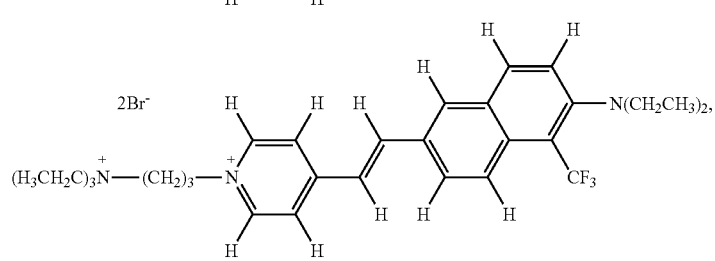
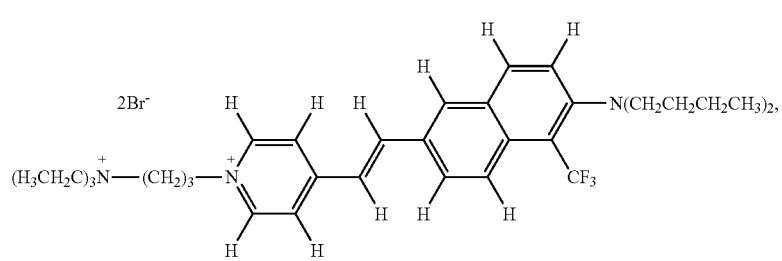

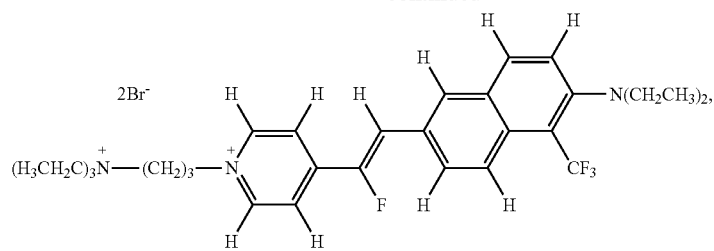
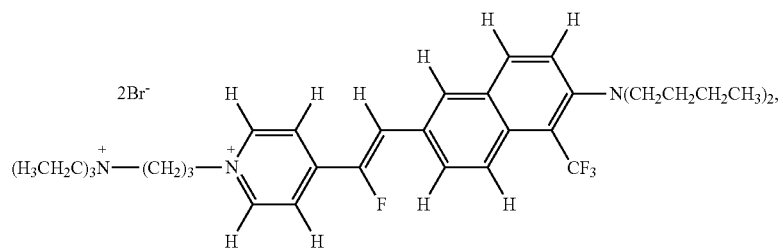
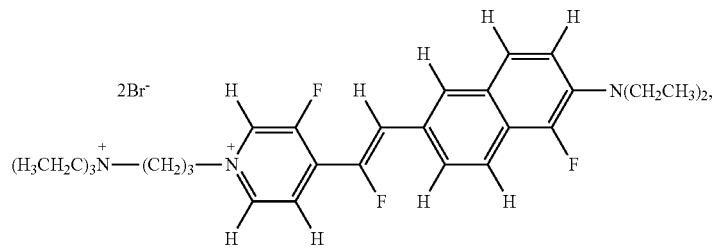
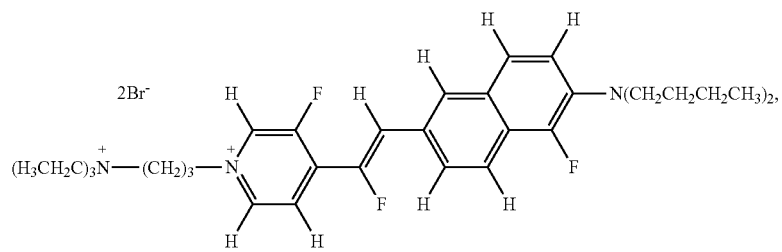
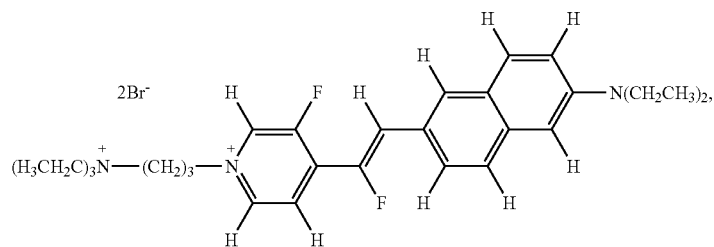
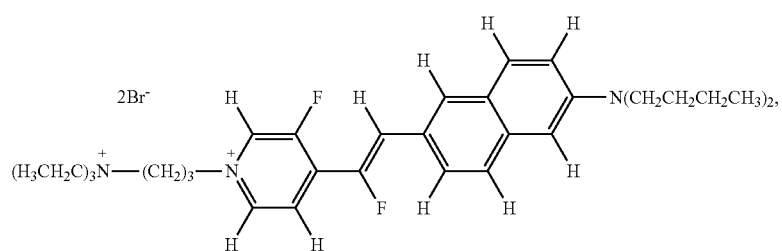

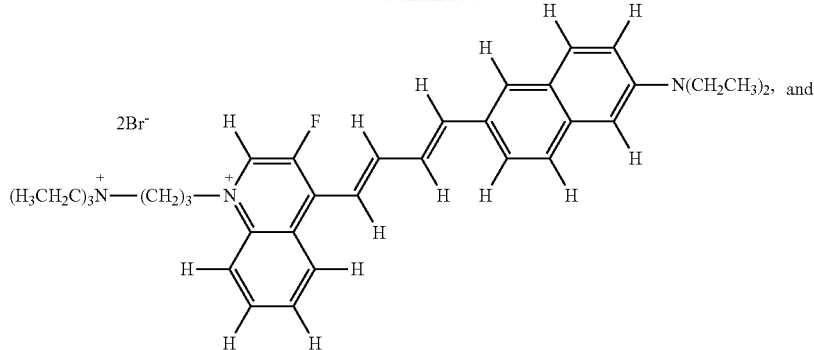
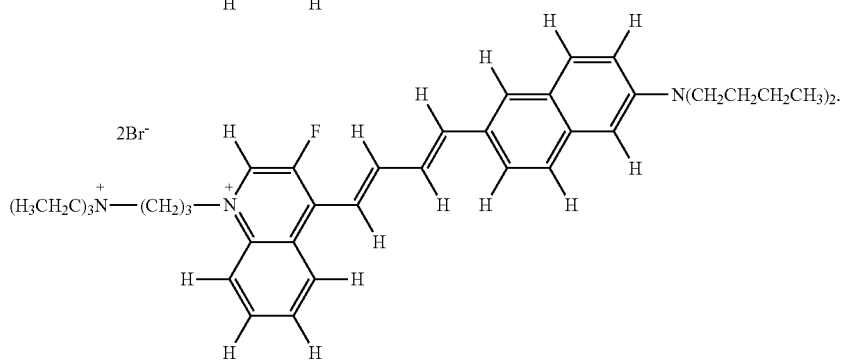
23. The fluorinated voltage sensitive dye of claim 1, selected from the group consisting of
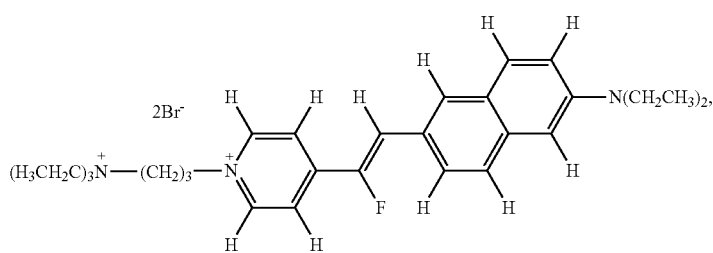
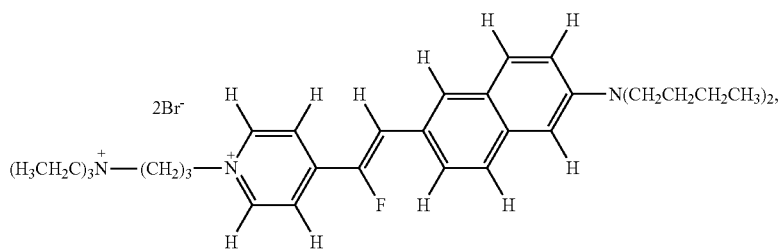
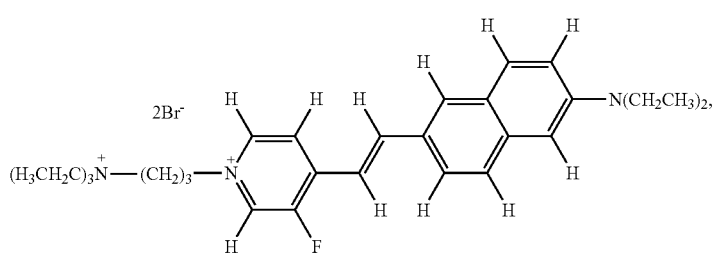

-continued
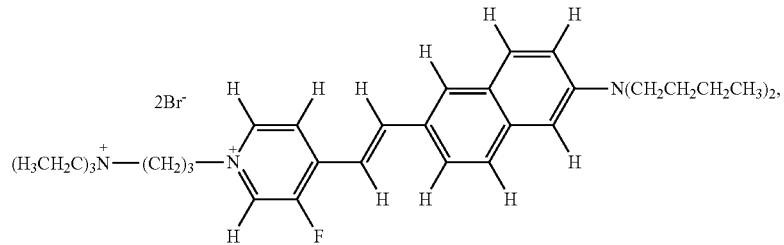
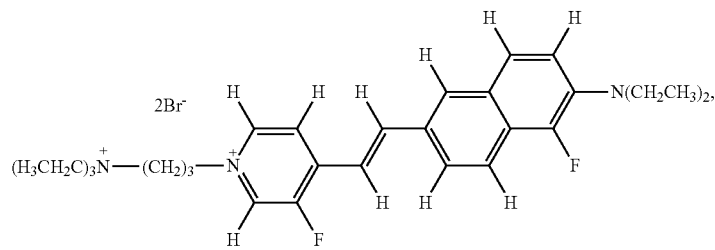
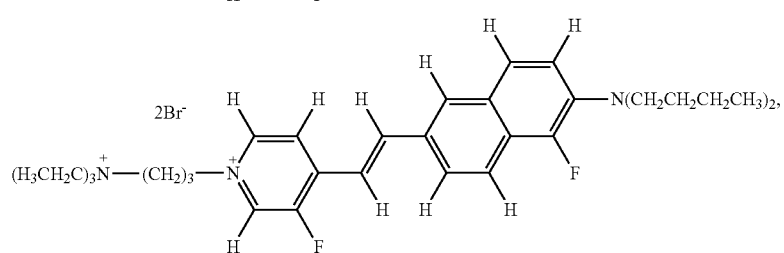
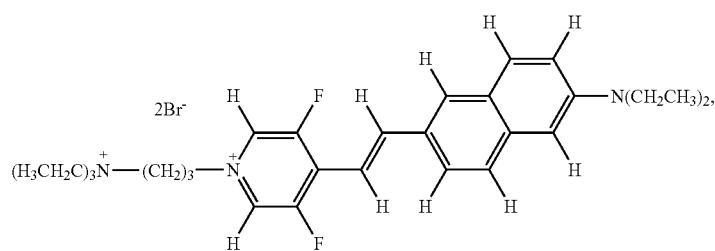
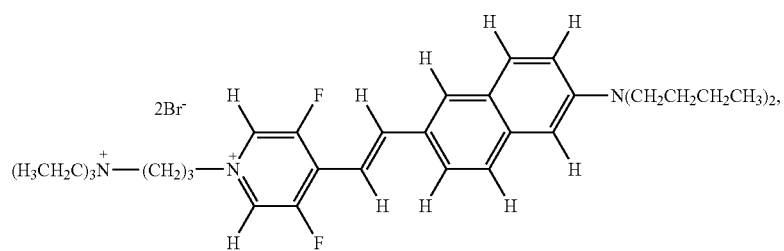
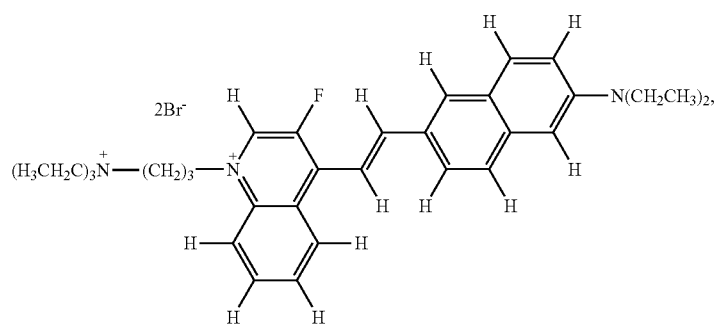

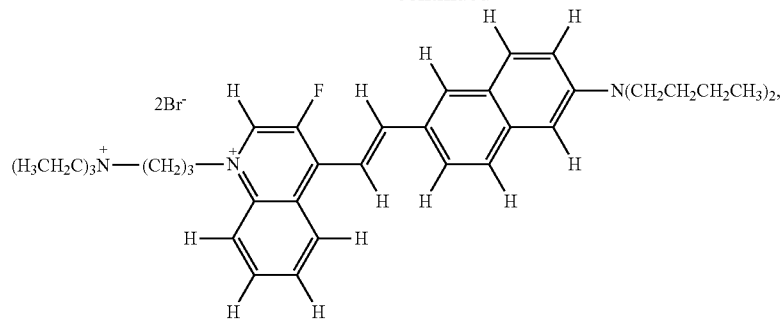
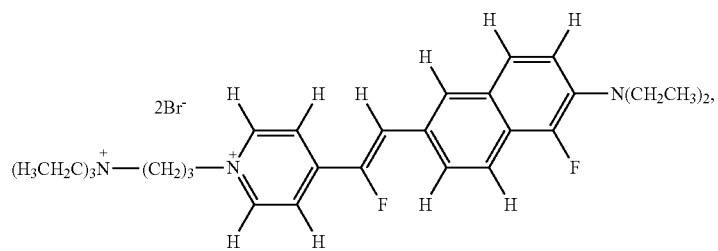
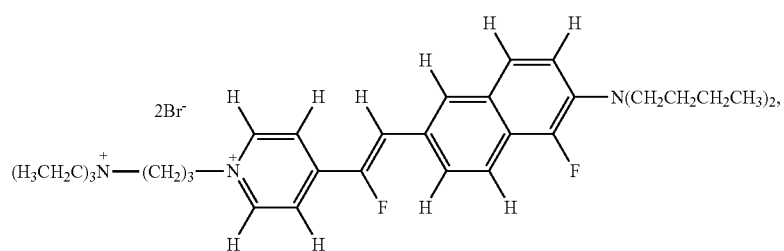
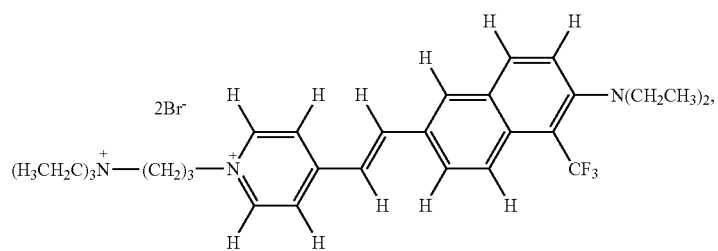
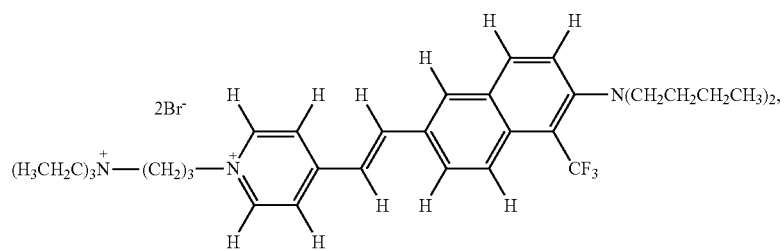
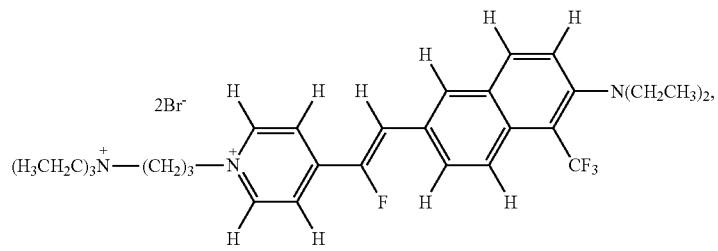

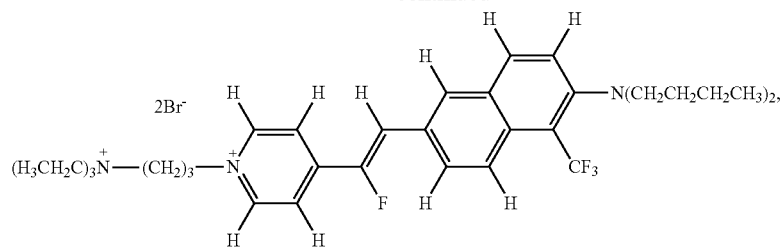
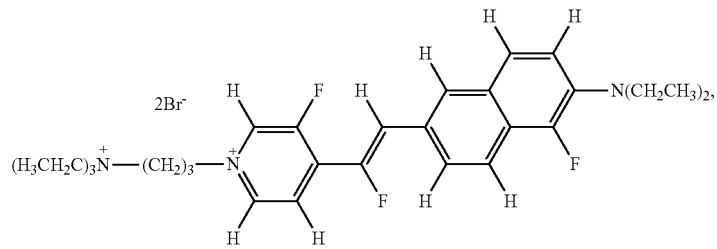
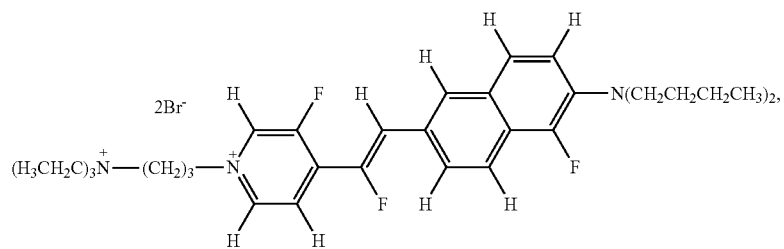
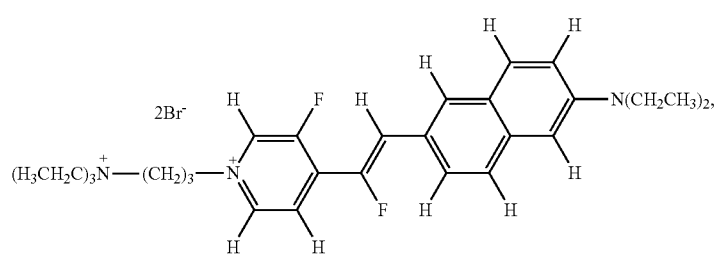
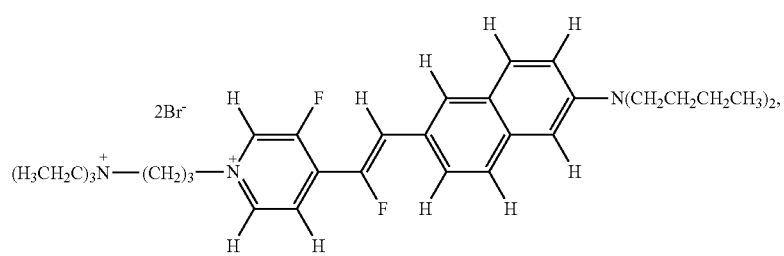
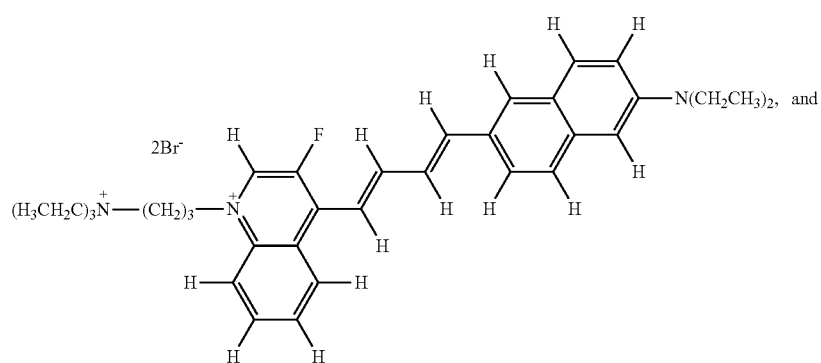

-continued

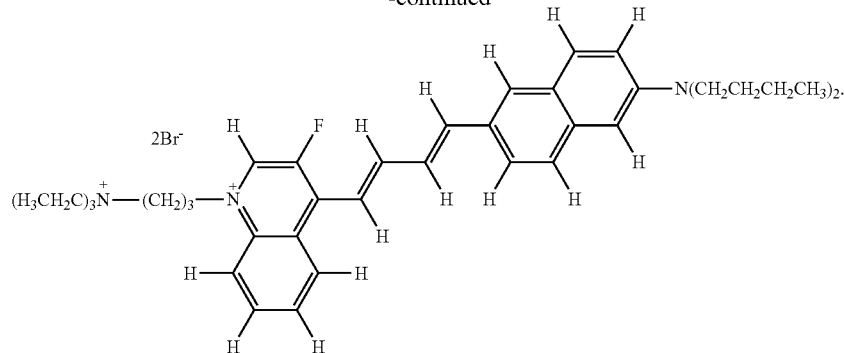

24. A method of forming a fluorinated voltage sensitive dye, the method comprising:

reacting a 1-(optionally substituted $C_1$-$C_{12}$ alkyl)-4-methylpyridinium compound and a 6-dialkylaminonaphthalene-2-carboxaldehyde to form the fluorinated voltage sensitive dye;

wherein the 1-(optionally substituted $C_1$-$C_{12}$ alkyl)-4-methylpyridinium compound has the structure

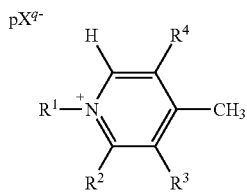

wherein p is 0, 1, or 2; $X^{q-}$ is an anionic counterion having a charge, q, that is 1 or 2; $R^1$ is an optionally substituted $C_1$-$C_{12}$ alkyl; $R^2$ is hydrogen, and $R^3$ is hydrogen or fluorine; or $R^2$ and $R^3$ collectively form a divalent —CH=CH—CH=CH— group; and $R^4$ is hydrogen or fluorine;

wherein the 6-dialkylaminonaphthalene-2-carboxaldehyde has the structure

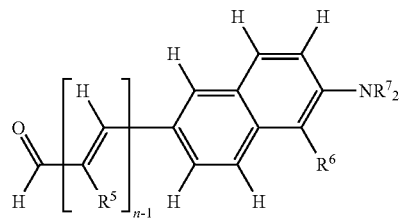

wherein n is 1 or 2; each occurrence of $R^5$ is independently hydrogen or fluorine; $R^6$ is hydrogen or fluorine or trifluoromethyl; and each occurrence of $R^7$ is independently $C_1$-$C_6$ alkyl; and wherein the fluorinated voltage sensitive dye is the fluorinated voltage sensitive dye of claim 1.

* * * * *